(12) United States Patent
Hyde et al.

(10) Patent No.: US 10,548,760 B2
(45) Date of Patent: Feb. 4, 2020

(54) CORRELATING A CONDITION OF A SUBJECT WITH A DEGREE OF SLEEP APNEA BEING EXPERIENCED BY THE SUBJECT

(71) Applicant: Elwha LLC, Bellevue, WA (US)

(72) Inventors: Roderick A. Hyde, Redmond, WA (US); Kenneth G. Caldeira, Redwood City, CA (US); Lowell L. Wood, Jr., Bellevue, WA (US); Dennis J. Rivet, Chesapeake, VA (US); Michael A. Smith, Phoenix, AZ (US)

(73) Assignee: Somne LLC, Bellevue, WA (US)

( * ) Notice: Subject to any disclaimer, the term of this patent is extended or adjusted under 35 U.S.C. 154(b) by 743 days.

(21) Appl. No.: 13/839,933

(22) Filed: Mar. 15, 2013

(65) Prior Publication Data

US 2014/0276174 A1    Sep. 18, 2014

(51) Int. Cl.
*A61B 5/08*        (2006.01)
*A61F 5/56*        (2006.01)
(Continued)

(52) U.S. Cl.
CPC ............ *A61F 5/56* (2013.01); *A61B 5/4818* (2013.01); *A61B 5/4836* (2013.01); *A61B 5/6822* (2013.01); *A61B 7/003* (2013.01); *A61H 9/0057* (2013.01); *A61M 16/0009* (2014.02); *A61M 16/0051* (2013.01); *A61M 16/0069* (2014.02);
(Continued)

(58) Field of Classification Search
CPC . A61M 16/00; A61M 16/0009; A61B 5/4818; A61B 5/4836; A61B 5/6822; A61F 5/56
See application file for complete search history.

(56) References Cited

U.S. PATENT DOCUMENTS

| 5,123,425 A | 6/1992 | Shannon, Jr. et al. |
| 5,199,424 A | 4/1993 | Sullivan et al. |

(Continued)

FOREIGN PATENT DOCUMENTS

WO     WO 03/006095 A1    1/2003

OTHER PUBLICATIONS

PCT International Search Report; International App. No. PCT/US2014/026122; Jul. 25, 2014; 4 pages.
(Continued)

*Primary Examiner* — Christian Jang
(74) *Attorney, Agent, or Firm* — Fogg & Powers LLC

(57) ABSTRACT

A system can perform the following procedure as part of a plan to treat sleep apnea, according to an embodiment. The system monitors a degree to which an airway of a subject is open, and monitors a condition that is related to the degree to which the airway is open. The system also correlates the condition to the degree to which the airway is open, and generates a data structure that represents the correlation between the condition and the degree to which the airway is open. This system can allow a sleep-apnea-treatment system to operate in a closed-loop mode, i.e., to monitor a level of sleep apnea in a subject by monitoring the correlated condition, and to treat the subject in a manner that the treatment system deems appropriate for the level of sleep apnea that the treatment system determines that the subject is experiencing.

20 Claims, 16 Drawing Sheets

(51) Int. Cl.
  *A61M 16/00* (2006.01)
  *A61B 5/00* (2006.01)
  *A61B 7/00* (2006.01)
  *A61H 9/00* (2006.01)
  *A61B 5/0205* (2006.01)

(52) U.S. Cl.
  CPC ......... *A61M 16/026* (2017.08); *A61B 5/0205* (2013.01); *A61B 5/0816* (2013.01); *A61H 2201/0207* (2013.01); *A61H 2201/0214* (2013.01); *A61H 2201/0285* (2013.01); *A61H 2201/165* (2013.01); *A61H 2201/1609* (2013.01); *A61H 2201/5007* (2013.01); *A61H 2201/5058* (2013.01); *A61H 2201/5071* (2013.01); *A61H 2201/5082* (2013.01); *A61H 2201/5084* (2013.01); *A61H 2201/5092* (2013.01); *A61H 2201/5097* (2013.01); *A61M 2205/15* (2013.01); *A61M 2205/332* (2013.01); *A61M 2205/3306* (2013.01); *A61M 2205/3368* (2013.01); *A61M 2205/3375* (2013.01); *A61M 2205/3606* (2013.01); *A61M 2205/3653* (2013.01); *A61M 2205/42* (2013.01); *A61M 2205/8206* (2013.01); *A61M 2210/1028* (2013.01); *A61M 2210/1032* (2013.01)

(56) References Cited

U.S. PATENT DOCUMENTS

| | | |
|---|---|---|
| 5,275,159 A | 1/1994 | Griebel |
| 5,309,921 A | 5/1994 | Kisner et al. |
| 5,343,878 A | 9/1994 | Scarberry et al. |
| 5,897,512 A | 4/1999 | Zagame |
| 6,062,216 A | 5/2000 | Corn |
| 6,349,724 B1 | 2/2002 | Burton et al. |
| 6,404,532 B1 * | 6/2002 | Berneth .................. G02F 1/161 359/265 |
| 6,468,234 B1 | 10/2002 | Van der Loos et al. |
| 6,609,517 B1 | 8/2003 | Estes et al. |
| 6,846,294 B2 * | 1/2005 | Rastegar ............. A61H 9/0078 601/11 |
| 6,877,513 B2 | 4/2005 | Scarberry et al. |
| 7,182,082 B2 | 2/2007 | Hoffrichter |
| 7,297,119 B2 | 11/2007 | Westbrook et al. |
| 7,762,263 B2 | 7/2010 | Aarestad et al. |
| 8,122,891 B2 | 2/2012 | Kimani Mwangi |
| 8,482,418 B1 | 7/2013 | Harman |
| 9,820,881 B2 | 11/2017 | Aarestad et al. |
| 10,092,442 B2 | 10/2018 | Aarestad et al. |
| 10,258,496 B2 | 4/2019 | Aarestad et al. |
| 2002/0002346 A1 | 1/2002 | Horst |
| 2002/0120207 A1 * | 8/2002 | Hoffman ............. A61B 5/0809 600/538 |
| 2003/0083702 A1 * | 5/2003 | Stadler .................... A61B 8/00 607/14 |
| 2003/0153956 A1 | 8/2003 | Park et al. |
| 2003/0167018 A1 | 9/2003 | Wyckoff |
| 2006/0266369 A1 | 11/2006 | Atkinson et al. |
| 2008/0114381 A1 * | 5/2008 | Voegele ................ A61B 17/10 606/151 |
| 2008/0163875 A1 | 7/2008 | Aarestad et al. |
| 2008/0243017 A1 * | 10/2008 | Moussavi ............. A61B 5/087 600/532 |
| 2009/0177124 A1 | 7/2009 | Silwa et al. |
| 2009/0234265 A1 | 9/2009 | Reid, Jr. et al. |
| 2010/0016767 A1 * | 1/2010 | Jones .................. A61M 1/0031 601/10 |
| 2010/0101583 A1 | 4/2010 | Chen et al. |
| 2010/0106117 A1 * | 4/2010 | Lockwood .......... A61M 1/0058 604/319 |
| 2010/0163043 A1 * | 7/2010 | Hart ..................... A61M 16/161 128/203.25 |
| 2010/0174250 A1 * | 7/2010 | Hu ........................ A61F 5/4401 604/319 |
| 2010/0275910 A1 | 11/2010 | Aarestad et al. |
| 2010/0277316 A1 | 11/2010 | Schlangen et al. |
| 2010/0294284 A1 | 11/2010 | Hohenhorst et al. |
| 2010/0298866 A1 * | 11/2010 | Fischvogt .......... A61B 17/0057 606/213 |
| 2011/0066086 A1 | 3/2011 | Aarestad et al. |
| 2011/0066123 A1 * | 3/2011 | Tout .................. A61F 13/00068 604/319 |
| 2011/0132378 A1 | 6/2011 | Levendowski et al. |
| 2012/0123286 A1 | 5/2012 | Wilson |
| 2012/0330204 A1 | 12/2012 | Baldauf et al. |
| 2013/0046181 A1 * | 2/2013 | Al-Abed ................ A61B 8/08 600/442 |
| 2013/0237793 A1 | 9/2013 | Farrugia et al. |
| 2014/0144450 A1 | 5/2014 | Aarestad et al. |
| 2014/0276252 A1 | 9/2014 | Hyde et al. |
| 2014/0296751 A1 | 10/2014 | Greenberg |
| 2015/0126912 A1 | 5/2015 | Scarberry |
| 2015/0142120 A1 | 5/2015 | Papay |
| 2016/0045356 A1 | 2/2016 | Grossman et al. |
| 2017/0367874 A1 | 12/2017 | Aarestad et al. |
| 2018/0028728 A1 | 2/2018 | Aarestad et al. |
| 2018/0125743 A1 | 5/2018 | Aarestad et al. |
| 2018/0177435 A1 | 6/2018 | Aarestad et al. |
| 2019/0021900 A1 | 1/2019 | Aarestad |
| 2019/0038453 A1 | 2/2019 | Aarestad et al. |
| 2019/0125572 A1 | 5/2019 | Aarestad et al. |
| 2019/0240065 A1 | 8/2019 | Aarestad et al. |

OTHER PUBLICATIONS

PCT International Search Report; International App. No. PCT/2018/013465; May 3, 2018; pp. 1-4.

* cited by examiner

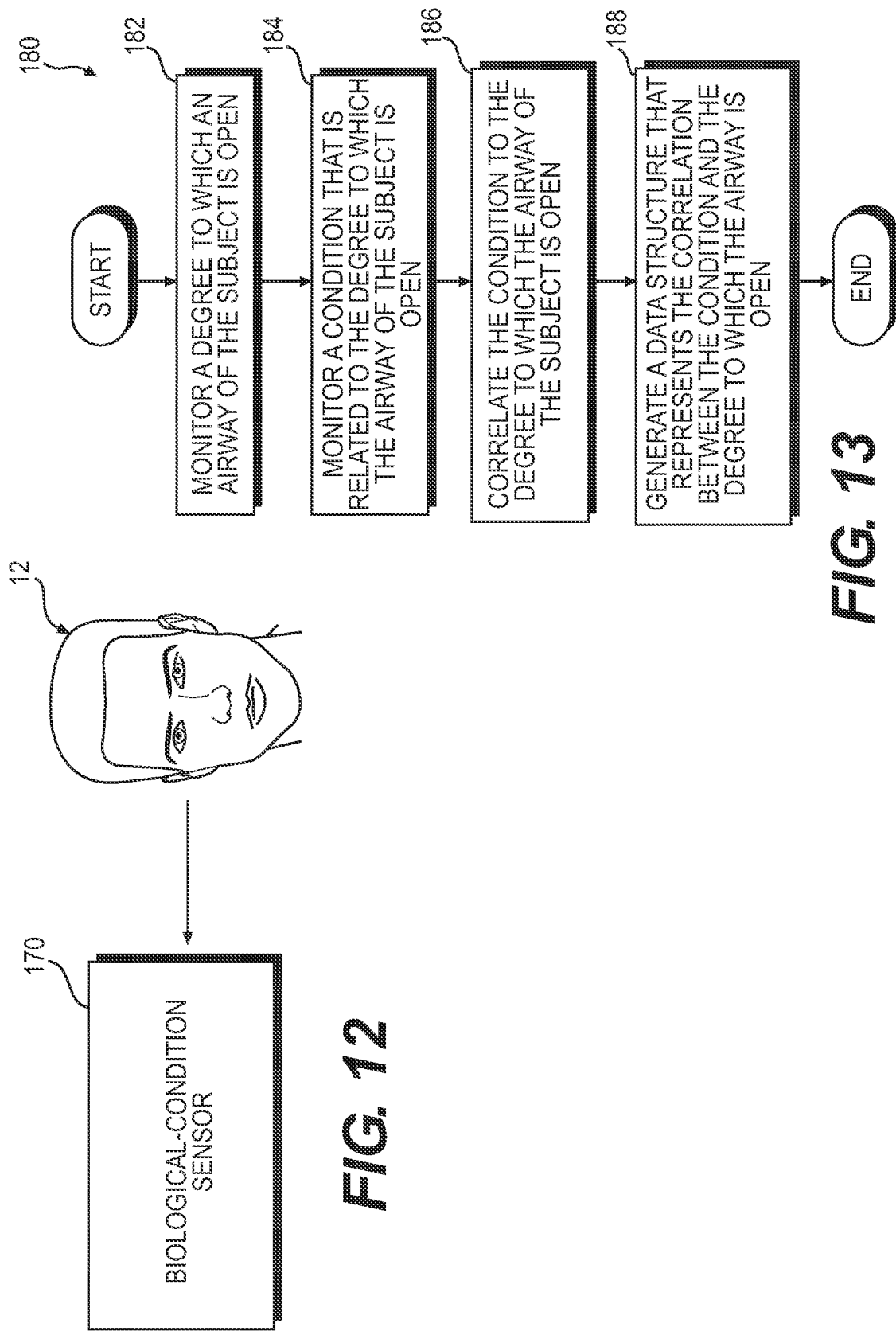

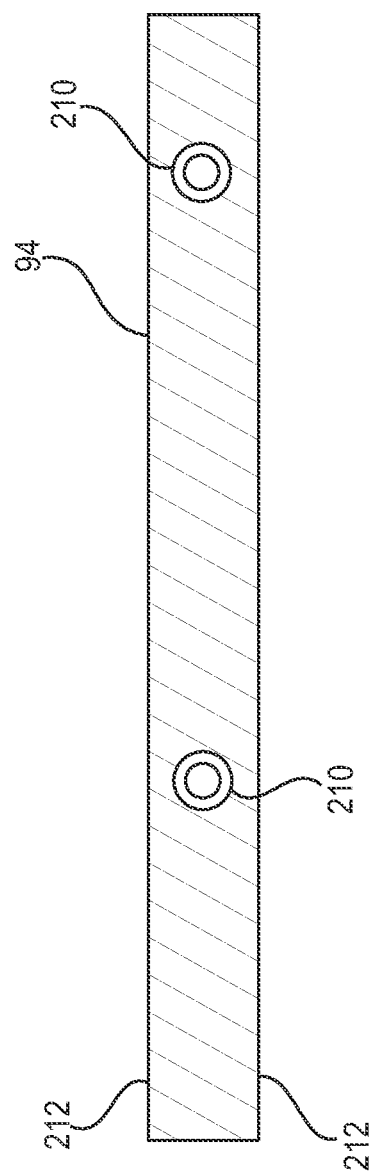

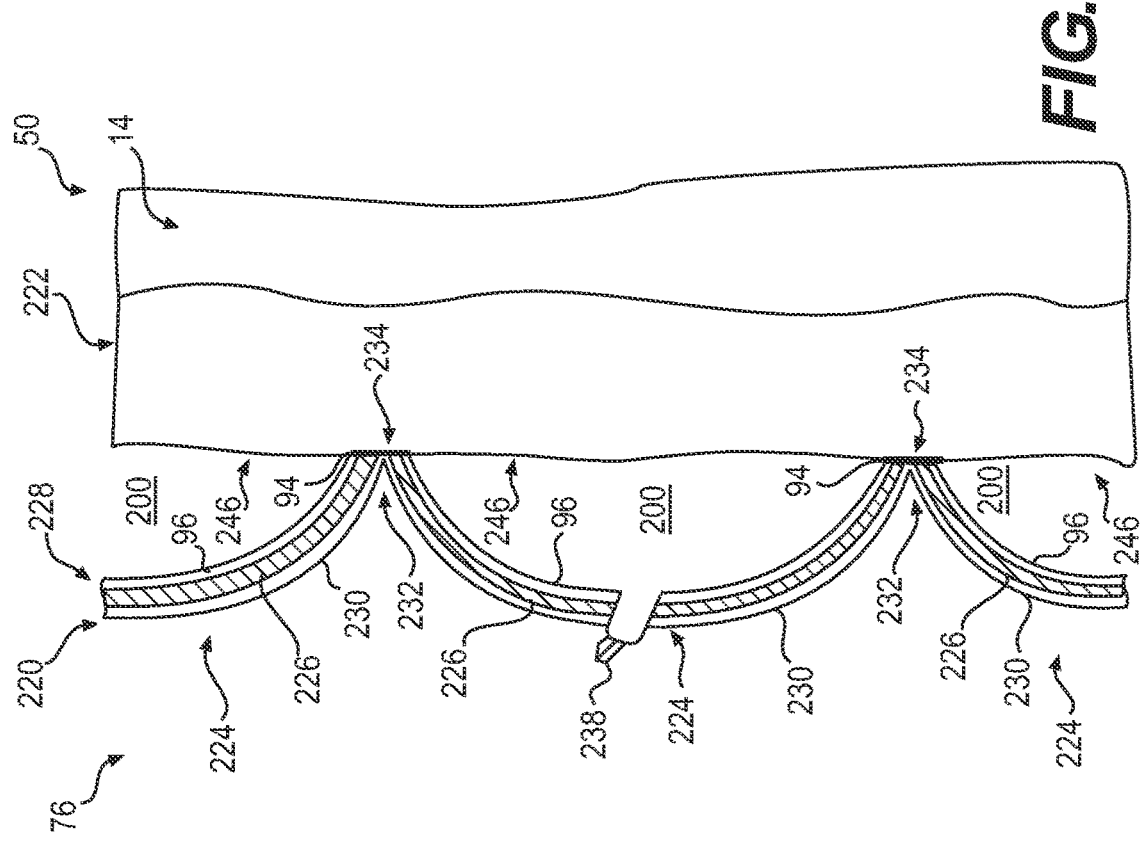
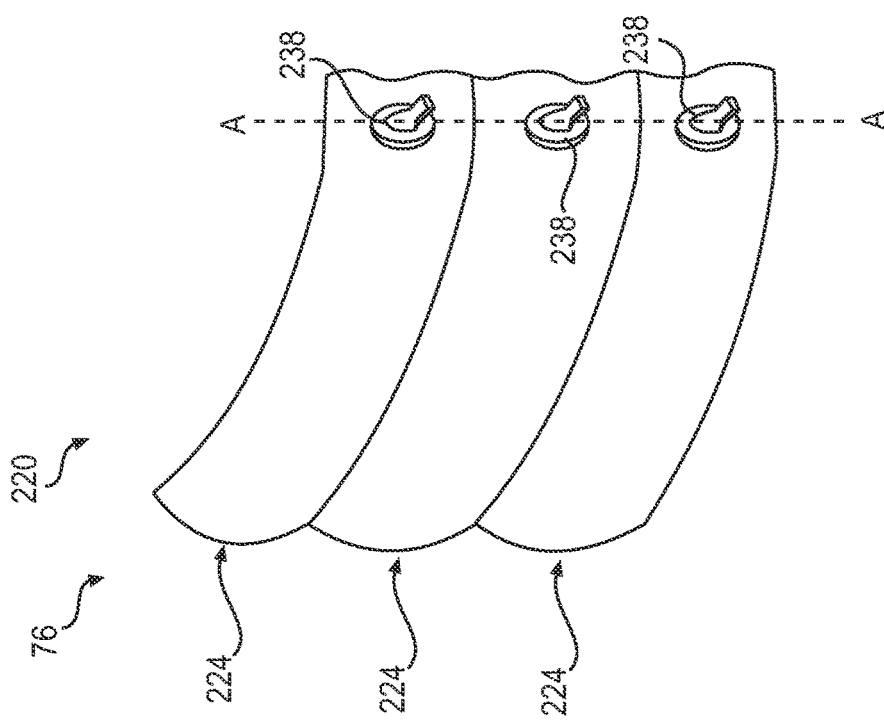

CORRELATING A CONDITION OF A SUBJECT WITH A DEGREE OF SLEEP APNEA BEING EXPERIENCED BY THE SUBJECT

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

RELATED APPLICATIONS

U.S. patent application Ser. No. 13/839,605, titled TREATING SLEEP APNEA WITH NEGATIVE PRESSURE, naming Roderick A. Hyde, Kenneth G. Caldeira, Lowell L. Wood Jr., Dennis J. Rivet, Michael A. Smith as inventors, filed Mar. 15, 2013, is related to the present application.

U.S. patent application Ser. No. 13/840,189, titled SLEEP-APNEA-TREATMENT SYSTEM THAT CHANGES THE TREATMENT PRESSURE OVER A PERIOD THAT BEGINS OR ENDS AT A SETTABLE TIME, naming Roderick A. Hyde, Kenneth G. Caldeira, Lowell L. Wood Jr., Dennis J. Rivet, Michael A. Smith as inventors, filed Mar. 15, 2013, is related to the present application.

U.S. patent application Ser. No. 13/840,374, titled SLEEP-APNEA-TREATMENT SYSTEM WITH MULTIPLE PRESSURE AND SEALING SURFACES, naming Roderick A. Hyde, Kenneth G. Caldeira, Lowell L. Wood Jr., Dennis J. Rivet, Michael A. Smith as inventors, filed Mar. 15, 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

A system can perform the following procedure as part of a plan to treat sleep apnea, according to an embodiment. The system monitors a degree to which an airway of a subject is open, and monitors a condition that is related to the degree to which the airway is open. The system also correlates the condition to the degree to which the airway is open, and generates a data structure that represents the correlation between the condition and the degree to which the airway is open.

The above-described system can allow a sleep-apnea-treatment system to monitor a level of sleep apnea in a subject by monitoring the correlated condition, and to treat the subject in a manner that the treatment system deems appropriate for the level of sleep apnea that the treatment system determines that the subject is experiencing. That is, the sleep-apnea-treatment system can be configured to operate in a closed-loop mode, in which the treatment system can adjust the level of treatment in response to the fed-back level of sleep apnea being experienced by the subject. In contrast, at least some existing sleep-apnea-treatment systems are configured to operate in an open-loop mode, in which the treatment system treats the sleep apnea according to a pre-configured treatment plan, and has no ability to adjust the treatment plan in response to the level of sleep apnea being experienced by the subject.

BRIEF DESCRIPTION OF THE FIGURES

FIG. 12 is a diagram of a portion of the apnea-degree-sensor assembly of FIG. 8, and of a subject, according to still another embodiment.

FIG. 13 is a flow diagram of a procedure for correlating a degree to which an airway of a subject is open to a condition that is related to the degree to which the airway is open, according to an embodiment.

FIG. 15 is a diagram of a sealing surface of the collars of FIGS. 4-7, according to another embodiment.

FIG. 16 is a diagram of a portion of a collar of FIGS. 4-7, according to an embodiment.

FIG. 17 is a view of the collar portion of FIG. 16 taken along line A-A of FIG. 16, according to an embodiment.

DETAILED DESCRIPTION

Figure 1:
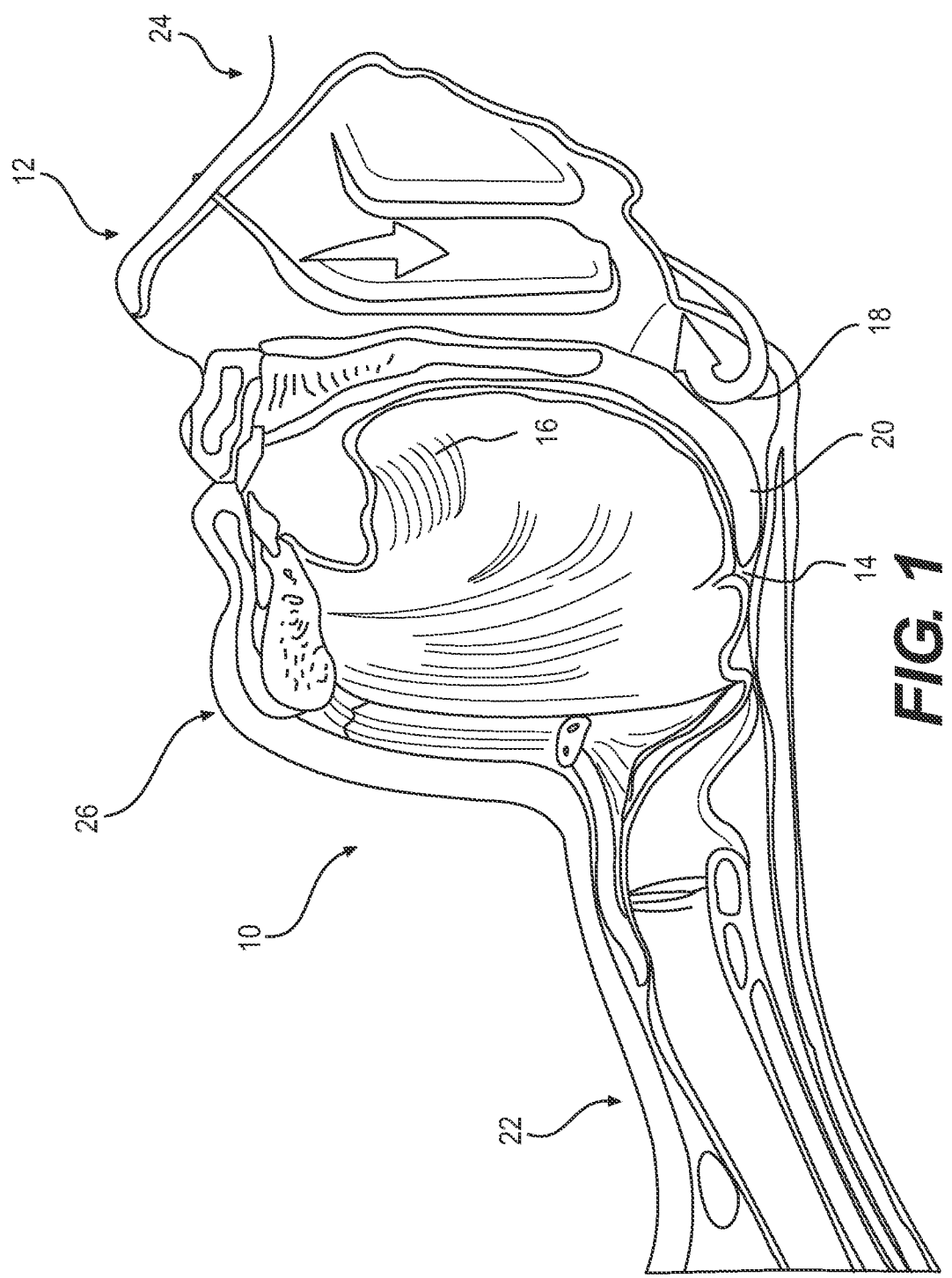
FIG. 1 is a diagram of an airway of a human subject, and of other biological tissues and structures near the airway.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more embodiments are described with reference to the drawings, wherein like reference numerals may be used to refer to like elements throughout. In the following description, for purposes of explanation, numerous specific details are set forth in order to provide a thorough understanding of the one or more embodiments. It may be evident, however, that one or more embodiments may be practiced without these specific details. In other instances, well-known structures and devices are shown in block-diagram form in order to facilitate describing one or more embodiments.

Sleep apnea is a disorder characterized by instances of abnormally low breathing, or by instances of abnormal pauses in breathing (e.g., "apneas"), during sleep; for example, such apneas can occur with a frequency of approximately 5-30 times or more per hour, and each apnea can last from approximately ten seconds to one or more minutes.

To prevent a subject who suffers from sleep apnea from suffocating during an apnea, the body produces a short "burst" of adrenaline, which burst typically rouses the subject enough to start him/her breathing again, but not enough to fully awaken him/her.

Unfortunately, these bursts of adrenaline can cause the subject to experience significant health problems. For example, because such bursts of adrenaline can stress the subject's heart by causing the subject's heart rate to increase relatively quickly, such bursts may increase the subject's risk of heart attack or stroke. Furthermore, because these bursts of adrenaline interrupt the subject's deep-sleep patterns, these bursts can be the underlying cause of health problems that are associated with a lack of sleep; examples of such lack-of-sleep-related health problems include an increase in non-lean body mass, arteriosclerosis, daytime fatigue, reduced cognitive function, reduced reaction time, and reduced attention span.

Because a subject suffering from sleep apnea is rarely aware of having difficulty breathing during sleep, or even after awakening, the subject may be unaware for many years that he/she suffers from sleep apnea until one or more symptoms, for example, in the form of one or more of the above-described health problems, manifest themselves to a degree that causes the subject to seek medical attention. But by then, the subject may have suffered serious injury (e.g., a heart attack), disability (brought on, e.g., by stroke), or even death (brought on, e.g., by the subject's failure to begin breathing after an apnea).

Consequently, proper treatment of sleep apnea can improve a subject's health in both the short term and in the long term, and, in some cases, can even prevent the subject's premature death.

The most common type of sleep apnea is obstructive sleep apnea.

FIG. 1 is a cut-away view of a head-and-neck region 10 of a subject 12.

Referring to FIG. 1, obstructive sleep apnea is characterized by an airway 14 of the subject 12 collapsing, i.e., becoming blocked during sleep by, e.g., the back of the tongue 16, the soft palate 18, or the uvula 20; therefore, each instance of a blocked airway typically causes an "apnea" as described above. Causes of a blocked airway 14 during sleep can include poor muscle tone in, over relaxation of, or excess tissue in, the tongue 16, soft palate 18, or uvula 20.

When the body of the subject 12 produces a burst of adrenaline during a block-airway-induced apnea to start the subject breathing again as described above, the adrenaline burst may unblock the airway 14 by causing the subject to, e.g., cough, move his/her neck 22, head 24, or jaw 26, or to breathe more deeply (the stronger suction caused by a deeper breath may force open the airway).

Then, after the subject 12 falls back into a deeper sleep, the muscles of the neck 22 and jaw 26 relax, the subject's respiratory rate returns to a deeper-sleep level, and, therefore, another cycle of an apnea followed by an adrenaline burst may commence.

Still referring to FIG. 1, there are many treatments available for obstructive sleep apnea.

Examples of invasive treatments include surgery to remove tissue from the body part (e.g., the tongue 16, soft palate 18, or uvula 20) responsible for the blockage of the airway 14, and surgery to implant one or more members into the blocking body part (e.g., to implant plastic rods into the soft palate) to "stiffen" the body part.

Unfortunately, potential problems with such invasive treatments include the risks, recovery time, irreversibility, and pain associated with a surgical procedure, including the risk that the procedure will cause the subject post-recovery discomfort when he/she swallows or while he/she is eating, and the risk that the procedure will ultimately prove unsuccessful in preventing reoccurrence of the airway blockages that cause obstructive sleep apnea.

And examples of non-invasive treatments include the subject 12 losing weight, using an oral appliance that maintains the subject's jaw 26 in a slightly protruding position during sleep, and using a Continuous Positive Airway Pressure (CPAP) machine, which is described below in conjunction with FIG. 2.

Although such non-invasive treatments are generally preferred over invasive treatments because, e.g., they can have fewer risks and side effects than invasive treatments, some non-invasive treatments, such as losing weight and using an oral appliance, may be ineffective for some subjects who suffer from obstructive sleep apnea.

But fortunately, it has been found that a CPAP machine can successfully treat obstructive sleep apnea in the majority of subjects who would otherwise suffer from it.

Figure 2:
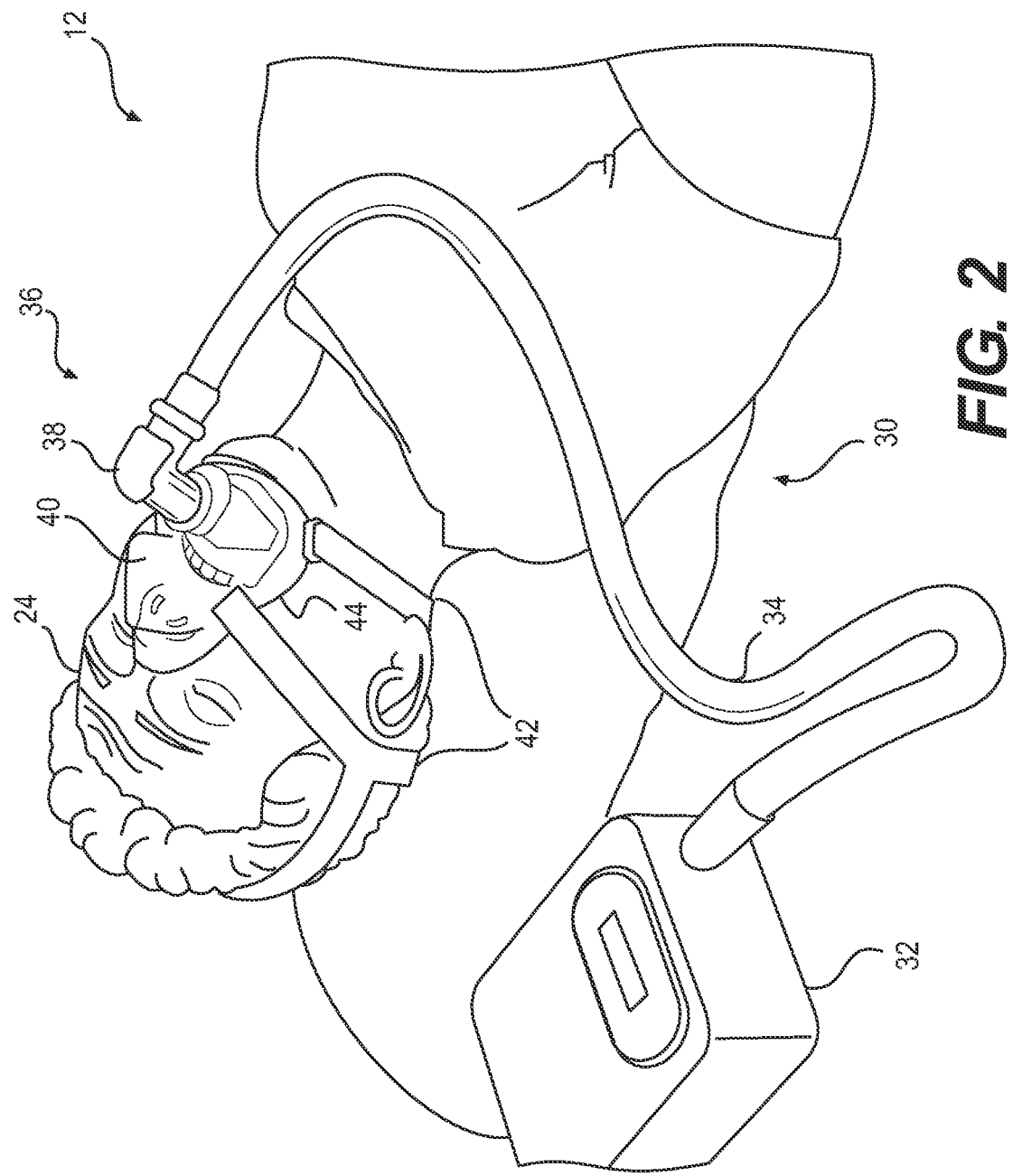
FIG. 2 is a diagram of a subject using a CPAP machine.

FIG. 2 is a view of a sleeping subject 12 using a CPAP machine 30 to prevent the occurrence of obstructive sleep apnea.

The CPAP machine 30 includes a base unit 32, a hose 34, and a mask assembly 36.

The base unit 32 is configured to maintain the air pressure within the hose 34, and thus within the airway 14 (FIG. 1) of the subject 12, at approximately constant levels while the subject is breathing in (inspiration) and while the subject is breathing out (expiration). If the CPAP machine 30 maintains the airway pressure at a different approximately constant level during inspiration than it does during expiration, then it is more properly called a BiPAP machine, although in common usage, "CPAP" is used to denote both a machine that maintains the airway pressure at the same level during inspiration and expiration and a machine that maintains the airway pressure at different levels during inspiration and expiration. The base unit 32 typically includes a power cord that plugs directly into a household power outlet (e.g., 110 VAC) or that is coupled to an AC adapter.

The hose 34 is configured to couple the base unit 32 to the mask assembly 36, and is typically long enough (e.g., six to ten feet) to allow the subject 12 to place the base unit on a floor or on a night stand while the subject is using the CPAP machine 30.

The mask assembly 36 includes a fitting 38, a mask 40, and straps 42. The fitting 38 is configured to couple the mask 40 to the hose 34, and may be coupled to the mask with a swivel joint that allows the subject 12 some freedom of movement. The mask 40 is configured to form an airtight seal 44 around at least the nose of the subject 12 (although the mask may also form a seal around the subject's mouth as shown in FIG. 2), and includes one or more openings (not shown in FIG. 2) that allow air to flow constantly from the base unit 32, through the hose 34 and fitting 38, into the mask 40, and out through the one or more openings, even during inspiration; without this constant airflow, the air inspired by the subject may become "stale." And the straps 42 secure the mask 40 to the head 24 of the subject 12 with a degree of tightness sufficient to form the airtight seal 44 between the mask and the face of the subject.

Still referring to FIG. 2, although, as described above, the CPAP machine 30 is an effective non-invasive treatment for obstructive sleep apnea, the CPAP machine may still have some shortcomings. For example, the nature of the hose 34 effectively tethering the mask assembly 36 to the base unit 32 may rob the subject 12 of his/her full range of movement during sleep. As an example, the subject 12 may be unable to roll to his/her left without causing the hose 34 to pull the base unit 32 off of a nightstand; or, if the base unit is on the floor, then the subject rolling to his/her left may cause the hose 34 to become taught and, therefore, to dislodge the mask 40 from the subject's face and break the seal 44. Furthermore, the subject 12 may be unable to sleep on his/her side without the pillow dislodging the mask 40 from the subject's face and breaking the seal 44. Moreover, the force with which the straps 42 must hold the mask 40 against the face of the subject 12 to form an airtight seal may cause discomfort to the subject. In addition, the CPAP machine 30 may prove inconvenient for travel, because, for example, when carrying the machine aboard an airplane, the subject 12 must separate at least the base unit 32 from other items while going through security, and the dimensions of the base unit may make it difficult for carrying in a briefcase or overnight bag.

Figure 3:
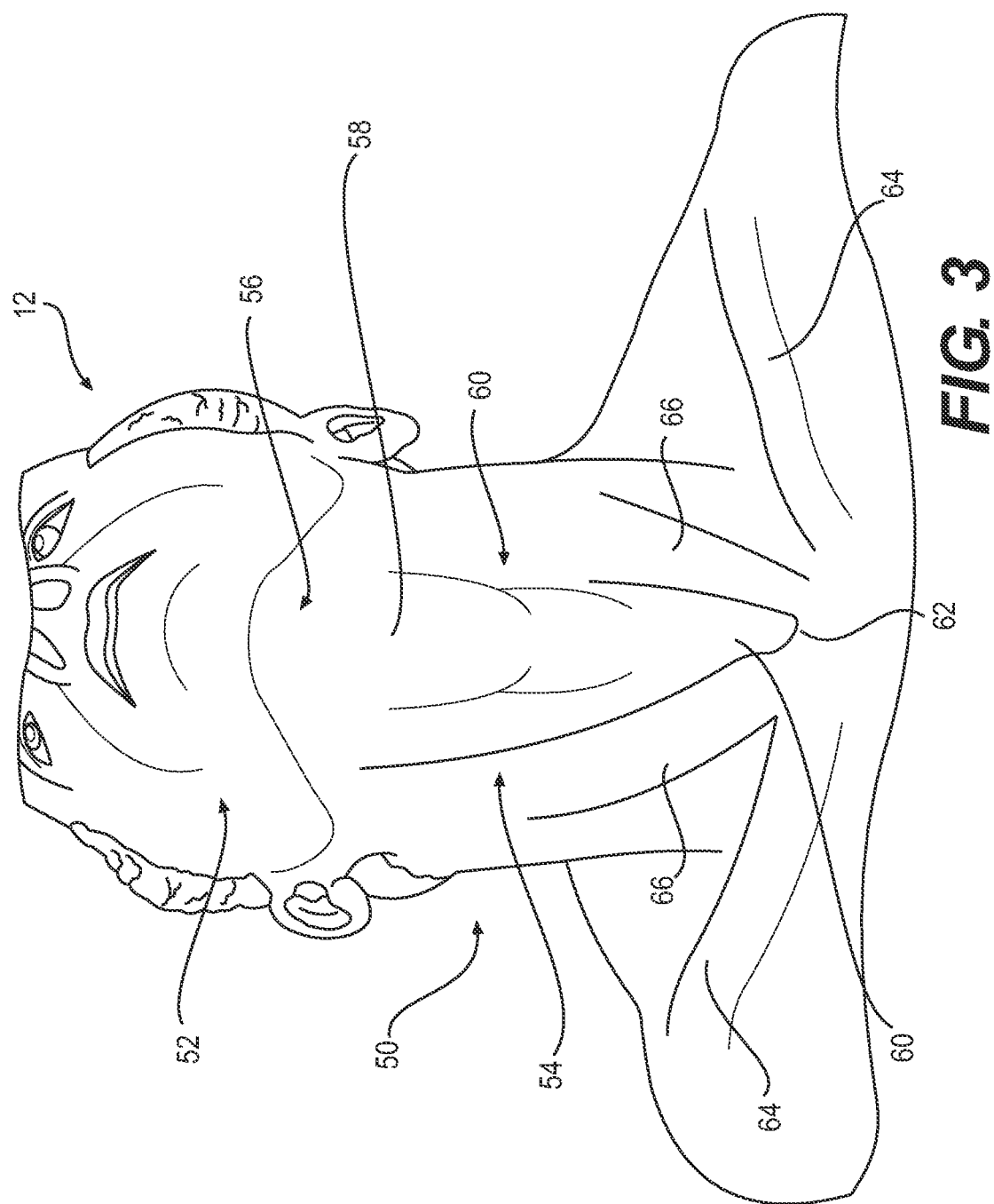
FIG. 3 is a diagram of a neck of a subject, and of a throat region of the neck.

FIG. 3 is a diagram of a neck 50 and a jaw 52 of a subject 12, and of a throat 54 of the neck.

Referring to FIG. 3, applying a negative pressure (i.e., suction or a vacuum) to one or more regions of the neck 50 and/or the jaw 52 of the subject 12 can treat obstructive sleep apnea non-invasively. For example applying a negative pressure to an underside 56 of the jaw 52, or to a region 58 of the throat 54 beneath the jaw, while the subject 12 is sleeping can assist to position the subject's jaw, tongue 16 (FIG. 1), or one or more other biological structures of the subject so to maintain the subject's airway 14 (FIG. 1) open. And, applying a negative pressure to one or more portions of a throat region 60 (which is below the throat region 58 and above the sternal head 62 and clavicle 64) while the subject 12 is sleeping can also position one or more biological structures of the subject 12 so as to maintain the subject's airway 14 open.

Figure 4:
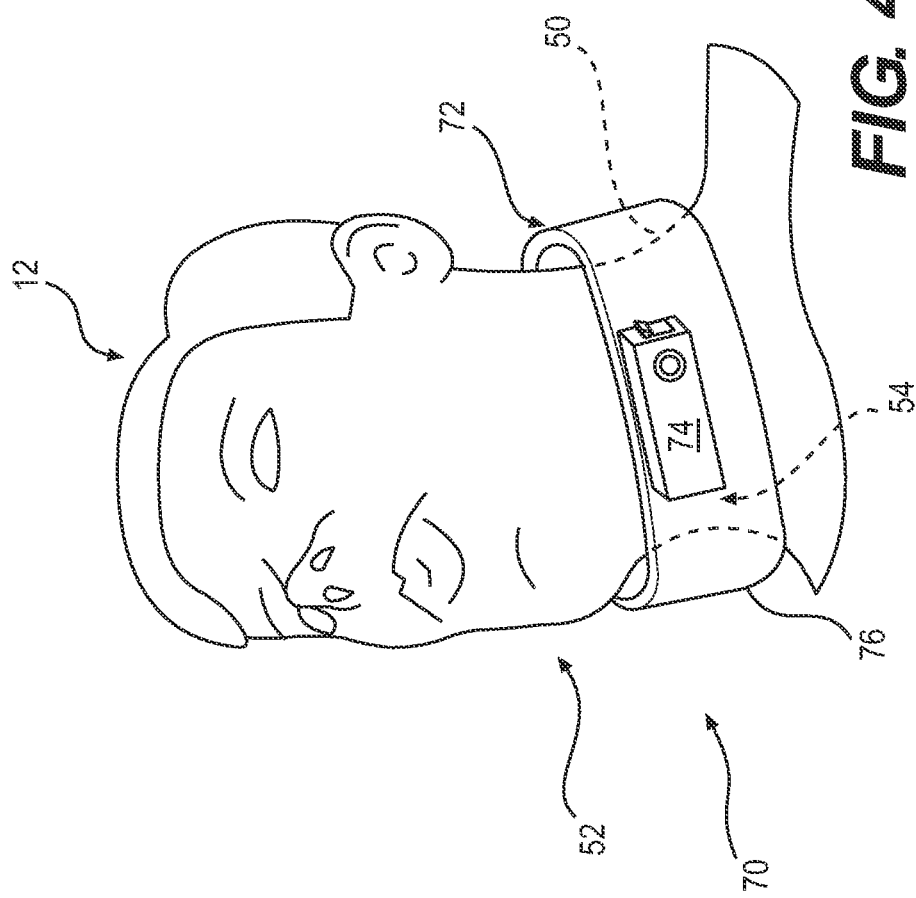
FIG. 4 is a view of a subject wearing a system for treating sleep apnea, according to an embodiment.

FIG. 4 is a diagram of a subject 12 using a negative-pressure sleep-apnea-treatment system 70, which is configured to treat obstructive sleep apnea, according to an embodiment. As described below in conjunction with FIGS. 5-22, the system 70 is self-contained, and is configured to maintain the subject's airway 14 (FIG. 1) open during sleep by applying and maintaining a negative pressure to one or more regions of the subject's neck 50, jaw 52, or throat 54. As used above, "self-contained" means that the system 70 is configured to treat obstructive sleep apnea by itself. As compared to a CPAP machine such as the CPAP machine 30 of FIG. 2, the system 70 can allow the subject 12 more freedom of movement because it is not tethered to any other item or location, can be more comfortable because it is worn around the neck and not over the face, and can be more suitable for travel because it can have fewer pieces, can be smaller, and can be foldable.

The negative-pressure sleep-apnea-treatment system 70 includes a collar assembly 72 and a component module 74, which is configured to be secured to the collar.

The collar assembly 72 includes a collar 76 and fasteners (not visible in FIG. 4), such as straps, snaps, buttons, or Velcro® strips, that are configured to secure the collar to the subject's neck 50 such that the collar forms an airtight seal around the one or more regions of the subject's neck, jaw 52, or throat 54 to which the system 70 is configured to apply a negative pressure. The collar 76 may be partially or fully flexible, may be formed from one or more suitable materials such as cloth, foam, metal, or plastic, and the collar or the fasteners may be configured to allow adjustment of the interior dimensions of the collar assembly 72 such that the assembly can fit subjects having a variety of neck circumferences, lengths, and shapes. The collar assembly 72 is further described below in conjunction with FIGS. 5-7.

And the module 74 is configured to include one or more components of the system 70 other than the collar assembly 72. For example, the module 74 can include an air pump, motor, power supply, pressure and airway sensors, and a controller. The module 74 is further described below in conjunction with FIG. 8.

Still referring to FIG. 4, alternate embodiments of the negative-pressure sleep-apnea-treatment system 70 are contemplated. For example, instead of being flexible, the collar 76 may include two or more rigid portions that are hinged together such that these portions are configured to open and receive the subject's neck 50, and then to close and attach around the neck. Furthermore, not all of the system components other than the collar assembly 72 may be disposed within the module 74. For example, some or all of these other components can be secured to the outside of the collar 76 or the outsides of the fasteners, can be secured to the inside of the collar or the insides of the fasteners, or can be disposed inside of the collar 76 or fasteners. Moreover, the module 74 and collar 76 may have any suitable shapes other than those shown in FIG. 4.

Figure 5:
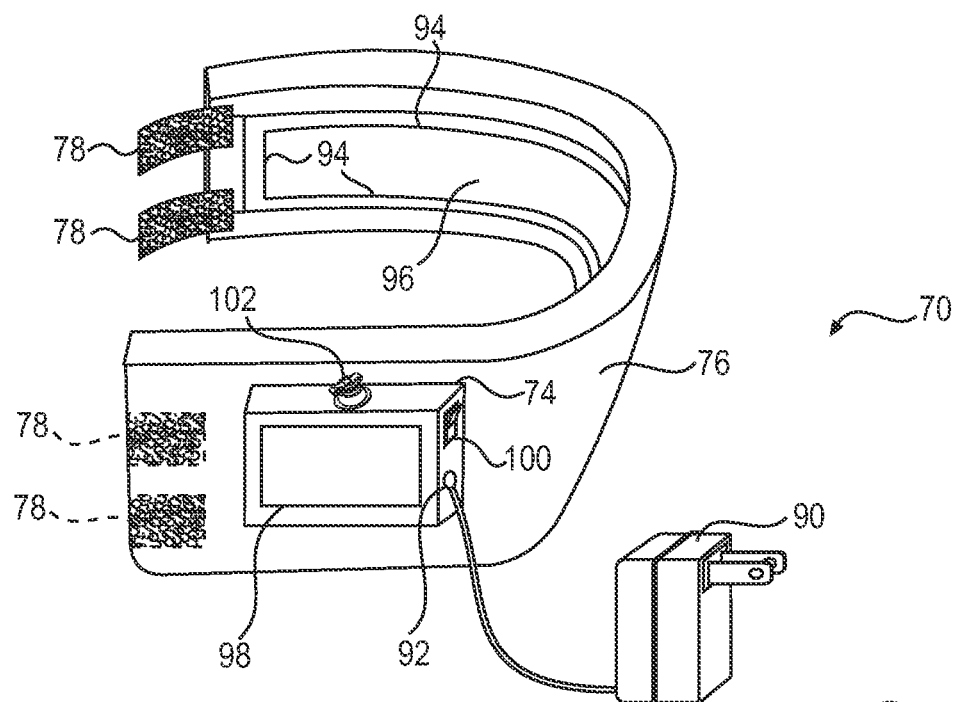
FIG. 5 is a view of a system for treating sleep apnea, according to an embodiment.

FIG. 5 is a view of the negative-pressure sleep-apnea-treatment system 70 of FIG. 4, according to an embodiment.

The collar 76 is a single, flexible piece that is configured to fully surround the subject's neck 50 (FIG. 4) while the subject wears the system 70, and the Velcro® fasteners 78 are adjustable so that the system 70 can fit a variety of neck sizes and shapes.

The system 70 also includes an AC adapter/charger 90, which is configured to couple to a receptacle 92 of the component module 74, and to power the system while the system is operating or to charge a battery (not shown in FIG. 5) of the system while the system is or is not operating. Alternatively, the receptacle 92 may be configured for coupling to a power cord that is configured for coupling to a standard power outlet (e.g., 110 VAC).

Furthermore, the system 70 includes one or more sealing surfaces 94, which are configured to form respective airtight seals with respective opposing regions of the subject's neck 50, and includes one or more vacuum surfaces 96, which are bounded by the sealing surfaces 94 and which are configured to sit opposite the regions of the subject's neck 50 (FIG. 4), jaw 52 (FIG. 4), or throat 54 (FIG. 4) to which the system applies a negative pressure. The one or more sealing surfaces 94 and the one or more vacuum surfaces 96 are further described below in conjunction with FIGS. 14-21.

Moreover, the component module 74 includes an input-output device 98, a power-switch assembly 100, and an air-outlet assembly 102. The input-output device 98 is, for example, a touch screen that allows the subject 12 (FIG. 4) to program, or otherwise to control, the system 70, and to receive information, such as status information and confirmation of programming, from the system 70. Alternatively, the input-output device 98 may include separate input (e.g., a keypad) and output (e.g., a display) devices. The power-switch assembly 100 is, for example, any suitable assembly that allows the subject 12 (FIG. 4) to turn the system 70 "on" or "off." And the air-outlet assembly 102 provides an outlet for the air that the system 70 sucks from between the collar 76 and the subject's neck 50 (FIG. 4), jaw 52 (FIG. 4), or throat 54 (FIG. 4) to create one or more regions of negative pressure between the collar and the neck, jaw, or throat.

Figure 6:
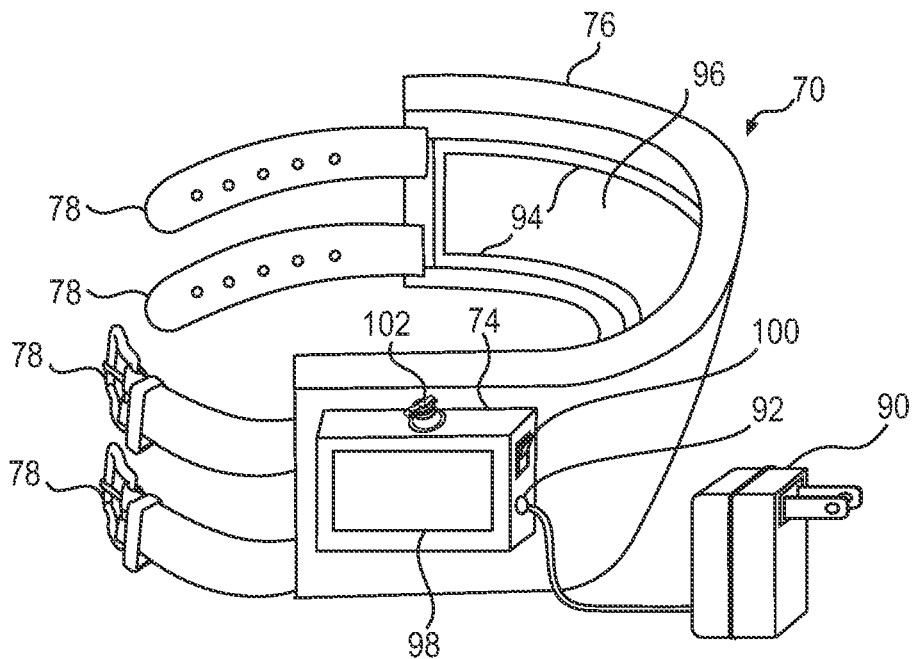
FIG. 6 is a view of a system for treating sleep apnea, according to another embodiment.

FIG. 6 is a view of the negative-pressure sleep-apnea-treatment system 70 of FIG. 4 according to yet another embodiment. The system 70 of FIG. 6 is similar to the system 70 of FIG. 5, except that the collar 76 is configured to surround the subject's neck 50 (FIG. 4) only partially when he/she wears the system, and the adjustable Velcro® fasteners 78 of FIG. 6 are longer than the fasteners 78 of FIG. 5 to compensate for the reduced length of the collar.

Figure 7:
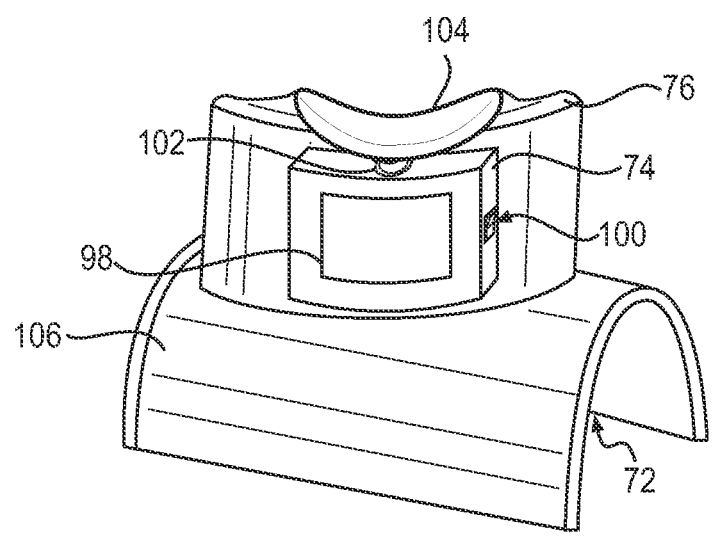
FIG. 7 is a view of a system for treating sleep apnea, according to yet another embodiment.

FIG. 7 is a view of the negative-pressure sleep-apnea-treatment system 70 of FIG. 4 according to still another embodiment. The system 70 of FIG. 7 is similar to the systems 70 of FIGS. 5-6, except that the collar 76 includes a portion 104, which is configured for positioning under the jaw 52 (FIG. 4) of the subject 12 (FIG. 4), and the system also includes a collar support 106. The collar 76 is configured to surround the neck 50 (FIG. 4) of the subject 12 (FIG. 4) only partially, and includes the portion 104, which is configured to allow for the application of negative pressure beneath the subject's jaw 52 (FIG. 4) or chin 26 (FIG. 1). And the collar support 106, which can take the place of, or be in addition to, the fasteners 78 of FIGS. 5 and 6, is configured to fit over the shoulders (not shown in FIG. 7) of the subject 12. The support 106 can be made of any suitable material that is flexible, rigid, or semi-rigid, and can have a design that affords the subject 12 freedom of movement while sleeping. And although not shown in FIG. 7, the system 70 of FIG. 7 may include one or more of the AC adapter 90, adapter receptacle 92, sealing surfaces 94, and vacuum surface 96, or any suitable alternatives thereof.

Referring to FIGS. 4-7, alternate embodiments of the sleep-apnea-treatment system 70 are contemplated. For example, the position of the component module 74 relative to the collar assembly 72 can be different than described. Furthermore, the positions of the input-output device 98, power switch 100, and air outlet 102 relative to the component module 74 may be different than described. Moreover, the collars 76 of FIGS. 4-6 may have chin or jaw portions that perform the same function as the portion 104 of FIG. 7. In addition, the system 70 may be modified any suitable manner.

Figure 8:
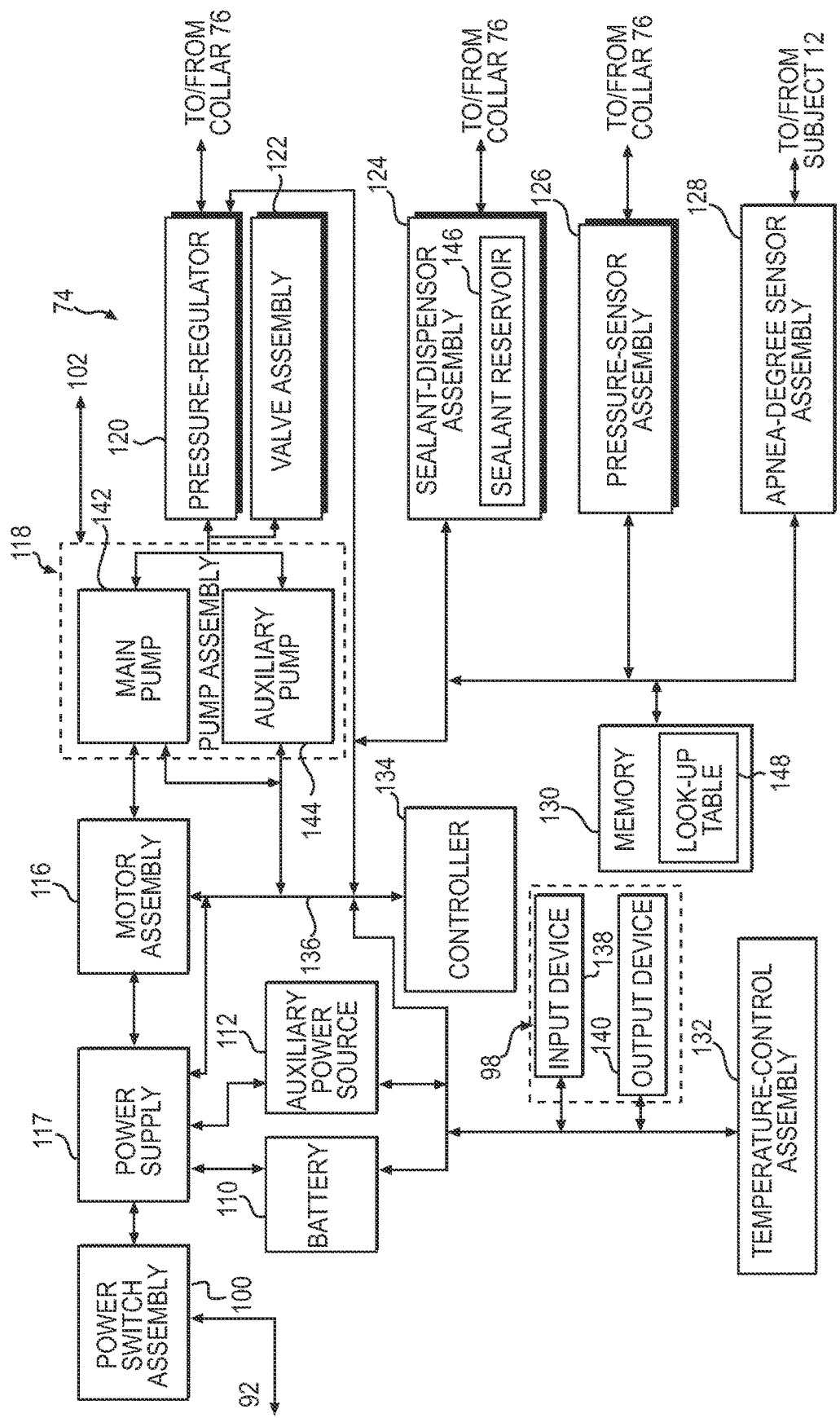
FIG. 8 is a block diagram of a component module of the sleep-apnea systems of FIGS. 4-7, according to an embodiment.

FIG. 8 is a block diagram of the component module 74 of FIGS. 4-7, according to an embodiment. In addition to the power receptacle 92, the input-output device 98, the power-switch assembly 100, and the air-outlet assembly 102, the component module 74 includes the following components: a battery 110, an auxiliary power source 112, a power supply 114, a motor assembly 116, a pump assembly 118, a pressure-regulator assembly 120, a valve assembly 122, a sealant-dispenser assembly 124, a pressure-sensor assembly 126, an apnea-degree-sensor assembly 128, a memory 130, a temperature-control assembly 132, a controller 134, and a bus 136. The module 74 may also include a package (not shown in FIG. 8) that houses these components. For example, the package may be formed from an epoxy resin and may be sealed to protect or to prevent access to the housed components, or may include a structure that allows access to one or more of the housed components for, e.g., repair or replacement. Furthermore, in addition to the power receptacle 92, the component module 74 may include other suitable receptacles or connectors that allow, e.g., airflow between the pressure-regulator assembly 120, the valve assembly 122, and the collar 76 (FIGS. 4-7), sealant flow between the dispenser assembly 124 and the collar, and signal communication to or from the sensor assemblies 126 and 128.

The power receptacle 92 is configured to receive a DC power signal, via the power-switch assembly 100, from, e.g., the AC adapter 90 (FIGS. 5-6), or is configured to receive an AC power signal from, e.g., a standard power outlet (e.g., 110 VAC).

The input-output device 98 is configured to receive data from, e.g., the subject 12 (FIG. 4), a sleep technician, or a sleep doctor, and to provide data to the subject, the technician, or the doctor. For example, the device 98 can be a touch screen that allows one to input data, and that displays data. Alternately, the device 98 may include a separate input device 138, such as a keypad or card reader, and a separate output device 140, such as a display screen or card writer. Examples of data that the one may input to the component module 74 via the device 98 include program instructions for the controller 134, and system-configuration and system-operating parameters such as pressure and temperature ranges and threshold levels.

The battery 110 is configured to store energy for powering the components of the component module 74, and for powering the negative-pressure sleep-apnea-treatment system 70 (FIGS. 4-7) in general. The battery 110 can be any suitable type of battery, such as a nickel-cadmium battery, a lithium-ion battery, or an alkaline battery, can produce any suitable output voltage (e.g., in a range of 5-25 VDC), and can be one-time usable or rechargeable. Furthermore, the battery 110 can include more than one battery or battery cell coupled together in electrical series, electrical parallel, or both electrical series and electrical parallel. Moreover, the battery 110 can provide an alarm (e.g., an alarm signal) to, e.g., the controller 134 or the input-output device 98, when the magnitude of the charge or voltage that the battery stores reduce to or below a low-charge threshold; alternatively, another component, e.g., the controller 134, can monitor the battery charge or voltage and generate such an alarm. In addition, the component module 74 may include a receptacle to hold the battery 110.

The auxiliary power source 112 is configured to generate energy for powering the components of the component module 74, and for powering the negative-pressure sleep-apnea-treatment system 70 (FIGS. 4-7) in general. For example, the auxiliary power source 112 can include a spring and a manual winding mechanism that the subject 12 (FIG. 4) can turn to wind the spring so as to store energy in the wound spring; as it unwinds, the spring is configured to drive an electrical generator (also included in the auxiliary power source) that is configured to generate a power signal. Or, the power source 112 can include an automatic winding mechanism that winds the spring in response to movement of the power source, such as when the subject 12 moves while wearing the system 70; such an automatic winding mechanism can be similar to a conventional mechanism used to wind a spring in a self-winding watch. Alternatively, the power source 112 can include a mechanism for automatically driving an electrical generator in response to movement of the power source; such a mechanism can be similar to a conventional mechanism used to drive an electrical generator in a self-powered watch. The auxiliary power source 112 can be configured to provide the power signal generated by the electrical generator directly to the power supply 114, or can be configured to charge the battery 110, or another battery that is part of the auxiliary power source, with the generated power signal.

The power supply 114 is configured to receive power from one or more of the receptacle 92 (via the power-switch assembly 100), the battery 110, and the auxiliary power source 112, and to convert this power into one or more currents and voltages that are suitable for powering itself, the other components of the module 74, and any other components of the system 70 (FIGS. 4-7). For example, the power supply 114 can be configured to sense a power signal at the receptacle 92, and to convert this sensed signal into one or more DC power signals having respective DC voltages. Furthermore, the power supply 114 can be configured to charge the battery 110 (and any battery in the auxiliary power source 112) while the power supply is receiving a power signal from the receptacle 92. The power supply 114 also can be configured such that if it does not sense a power signal at the receptacle 92, then it converts a power signal from the auxiliary power source 112 into the one or more DC power signals, and uses any excess power (i.e., a level of power above what is needed to power the components of the sleep-apnea-treatment system 70) from the auxiliary power source to charge the battery 110 (and any battery in the auxiliary power source 112). Further, the power supply 114 can be configured such that if it does not sense a power signal at the receptacle 92 and it senses that the power from the auxiliary power source 112 is insufficient to meet the power demands of the system 70, then it converts a power signal from the battery 110 into the one or more DC power signals, and uses any power from the auxiliary power source to charge the battery. The power supply 114 can be or include any suitable type of power supply, for example, a DC-DC converter such as a buck converter, a boost converter, or a buck-boost converter.

The motor assembly 116 includes one or more motors that are configured to convert electrical energy in the form of a power signal from the power supply 114 into mechanical energy for driving one or more pumps of the pump assembly 118. For example, the motor assembly 116 may include any suitable electrical motor such as a DC motor, a brushless DC motor, a brushed AC synchronous motor, or an induction motor. Furthermore, the motor assembly 116 may include a motor-controller circuit for converting the power signal from the power supply 114 into one or more suitable signals for driving, commutating, and otherwise controlling, the one or more motors. Moreover, the motor assembly 116 can include one or more structures that are configured for cooling the one or more motors, arresting, or otherwise compensating for, vibrations generated by the one or more motors, or muffling sounds generated by the one or more motors so that the motor assembly does not disturb the subject 12 (FIG. 4) while he/she is sleeping.

The pump assembly 118 includes a main pump 142, which is configured to generate a respective negative pressure within each pressure region—a pressure region is further described below in conjunction with FIGS. 14-21— between the collar 76 (FIGS. 4-7) and the neck 50 (FIG. 4) of the subject 12 (FIG. 4) while being driven by the motor assembly 116, and includes an auxiliary pump 144, which is configured to operate independently of the motor assembly. For example, the pump assembly 118 can be mechanically coupled to the motor assembly 116 with, e.g., one or more shafts and transmissions. The main pump 142 can be any suitable fluid pump or compressor, such as an impeller pump or a piston pump. And, like the main pump 142, the auxiliary pump 144 can be any suitable fluid pump or compressor, such as an impeller pump or a piston pump; but unlike the main pump, the auxiliary pump is configured to be drivable independently of the motor assembly 116. For example, the auxiliary pump 144 can include, and can be drivable by, a manual- or self-winding spring mechanism that can be similar to the spring mechanism described above in conjunction with the auxiliary power source 112. Or, the auxiliary pump 144 can include, and can be drivable by, a self-electrical-generator mechanism that can be similar to the self-electrical-generator mechanism described above in conjunction with the auxiliary power source 112.

The pump assembly 118 is configured to engage the main pump 142 while the power supply 114 is providing enough power to operate the motor assembly 116, and to engage the auxiliary pump 144, alone or together with the main pump, while the power supply is not providing enough power to operate the motor assembly. Consequently, the pump assembly 118 is configured to generate a negative pressure even in the absence of power from the supply 114.

The air that the pump assembly 118 pumps from the pressure regions between the collar 76 (FIGS. 4-7) and the subject's neck 50 (FIG. 4) to create the respective negative pressures exits the pump assembly via the air outlet 102.

Furthermore, although described as including a single main pump 142 and a single auxiliary pump 144, the pump assembly 118 may include multiple main pumps or multiple auxiliary pumps.

The pressure-regulator assembly 120 and the valve assembly 122 are configured to cooperate to provide a respective negative pressure to each of one or more pressure regions between the neck 50 (FIG. 4) of the subject 12 (FIG. 4) and the collar 76 (FIG. 4), and to regulate these one or more pressures. The valve assembly 122 includes one or more valves that are configured to direct one or more negative pressures to one or more respective pressure regions between the collar 76 (FIGS. 4-7) and the neck 50 (FIG. 4), and the pressure-regulator assembly 120 includes one or more pressure regulators coupled to the valves and configured to regulate these one or more negative pressures to respective pressure levels. For example, the one or more valves can each be one-way valves that allow air to flow from the collar 76 toward the pump assembly 118. And the one or more pressure regulators can each be mechanical, open-loop regulators that bypass any air drawn by the pump assembly 118 in excess of the level of drawn air needed to maintain each of the one or more negative pressures at a respective level. Or, each pressure regulator can employ feedback to the pump assembly 118 or the motor assembly 116, either directly or via the controller 134, to regulate the respective pressures by controlling the pumping power. Furthermore, the one or more pressure regulators and one or more valves can be coupled to each other and to the pressure regions between the collar 76 and the neck 50 via a suitable network of hoses and couplings, which can be part of one or both of regulator and valve assemblies 120 and 122, or which can be separate from these assemblies. Moreover, a pressure regulator of the regulator assembly 120 can be configured to detect an air leak in a pressure region between the collar 76 and the neck 50, and to instruct the sealant dispenser 124, directly or via the controller 134, to dispense a sealant in the vicinity of the air leak in an effort to seal the leak. In addition, one or more of the pressure regulators can each be configured to limit the magnitude of the negative pressure in a respective pressure region to a threshold pressure level that has been determined to be approximately the maximum safe limit for the subject 12. Furthermore, the regulator and valve assemblies 120 and 122 may form part, or all, of a rapid-re-pressurization assembly that is configured to quickly remove the application of negative pressure to the neck 50 of the subject 12 by rapidly increasing the pressure within one or more of the pressure chambers. This rapid re-pressurization may serve to prevent discomfort or injury to the subject 12, and may be manually activated by the subject (e.g., by an emergency or panic button or a voice command) or may be triggered by a sensor in response to, e.g., detecting respiratory-distress sounds abnormal heart activity, or a low blood-oxygen level). And this rapid re-pressurization can include stopping one or more of the pumps of the pump assembly 118, opening a valve (e.g., an emergency valve) or breaking a seal between the neck 50 and one or more sealing surfaces 94 to allow ambient air to enter the one or more of the pressure regions, or taking one or more similar actions.

The sealant-dispenser assembly 124 includes a sealant reservoir 146, and is configured to dispense a sealant from the reservoir to, or near, one or more sealing surfaces 94 (FIGS. 5-6 and 14-15) for the purpose of facilitating, fortifying, and/or repairing an airtight seal between a sealing surface and the neck 50 (FIG. 4) of the subject 12 (FIG. 4). For example, the dispenser assembly 124 can include on or more sealant pumps that can be similar to one or both of the pumps 142 and 144 of the pump assembly 118. Furthermore, the dispenser assembly 124 can include one or more pumps or other structures configured to pressurize the reservoir 146, to apply force to (e.g., squeeze) the reservoir, to push the sealant from the reservoir via a piston, or to take one or more similar actions, so as to transport the sealant from the reservoir. Moreover, the dispenser assembly 124 can be coupled to the reservoir 146 and to the collar 76 via a suitable network of hoses, couplings, and ejection nozzles; these components may be part of, or separate from, the dispenser assembly.

The sealant held in the reservoir 146 can be any suitable substance such as a liquid, gel, cream, or foam that forms a flexible or rigid seal and that does not irritate the subject's skin; examples of such gels include silicone-based gels. Furthermore, the sealant can be configured to form a second seal separate from the seal formed by the sealing surfaces 94 (FIGS. 5-6).

For example, if a pressure regulator of the assembly 120, or a pressure sensor of the assembly 126, senses a leak in one of the pressure regions (described below in conjunction with FIGS. 14-21), then the pressure regulator can instruct the dispenser assembly 124, directly or via the controller 134, to dispense the sealant held in the reservoir 146 at or near one or more of the sealing surfaces 94 (FIGS. 5-6 and 14-15) that border the pressure region. For example, the pressure regulator can be configured to instruct the dispenser assembly 124 to dispense the sealant successively via each sealant-dispense nozzle (e.g., described below in conjunction with FIG. 15) near the one or more sealing surfaces 94 that border the pressure region until the pressure regulator detects that the leak has slowed or stopped. The controller 134, pressure-regulator assembly 120, or another one or more components of the component module 74, can be configured to detect a leak in a pressure region in one or more of the following manners: determining that the speed of a pump within the pump assembly 118 exceeds a threshold level, determining that the energy consumed, or the heat generated, by the pump assembly 118 exceeds a threshold level, determining that the airflow level through the pump assembly exceeds a flow or leak threshold, or by detecting a space between a sealing surface 94 and portion of the subject's neck 50 (FIG. 4) opposite the sealing surface.

The pressure-sensor assembly 126 is configured to generate, and to provide to the controller 134, a respective indication (e.g., a feedback signal) of the pressure in each of the one or more pressure regions formed between the collar 76 (FIG. 4) and the neck 50 (FIG. 4) of the subject 12 (FIG. 4). For example, the pressure-sensor assembly 126 can include a respective pressure sensor in each pressure region, or in an air hose coupled to each pressure region. In response to these pressure indications, the controller 134 can be configured to control the pump assembly 118, the pressure-regulator assembly 120, or the valve assembly 122 to maintain the pressure in each pressure region at a respective programmed or otherwise set, level. Furthermore, if the controller 134 determines that there is a leak in one of the pressure chambers, then the controller can be configured to control the sealant-dispenser assembly 124 to dispense a sealant as described above in an attempt to seal the leak. Moreover, if the controller 134 determines that a pressure in a pressure region has exceeded a threshold pressure level, such as a safety threshold pressure level, then the controller can control the pump assembly 118, the pressure-regulator assembly 120, or the valve assembly 122 to maintain the pressure within the pressure region at or below the safety threshold pressure level. In addition, in response to the one or more pressure indications from the pressure-sensor assembly 126, the controller 134 can implement a peristalsis procedure as described below in conjunction with FIGS.

16-18. In other words, the pump assembly 118, the pressure-regulator assembly 120, the valve assembly 122, the pressure-sensor assembly 124, and the controller 134 form at least part of a feedback loop for maintaining the respective pressure within each of the one or more pressure regions within a respective programmed, or otherwise set, range; alternatively, at least the controller 134 can be omitted from this feedback loop. Furthermore, the pressure-sensor assembly 126 can be configured to perform at least some of the functions of the pressure-regulator assembly 120, and, therefore, can be configured to provide redundancy for these functions. Alternatively, the pressure-sensor assembly 126 can be configured to perform some pressure-related functions, and the pressure-regulator assembly 120 can be configured to perform other pressure-related functions; for example, the pressure-regulator assembly 120 can be configured to prevent the magnitude of the pressure within any pressure region from exceeding a safety threshold pressure level, and the pressure-sensor assembly 126 can be configured to perform all other pressure-related sensing functions.

The apnea-degree-sensor assembly 128 is configured to generate and to provide to the controller 134, an indication of the degree of sleep apnea being experienced by the subject 12 (FIG. 4) while he/she is sleeping. For example, the apnea-degree-sensor assembly 128 can include one or more sensors that are configured to generate an indication of the degree to which the subject's airway 14 (FIG. 1) is open. In response to this indication, the controller 134 is configured to control the pump assembly 118 or the pressure-regulator assembly 120 to change the pressure in at least one pressure region in a manner that lessens the degree of sleep apnea being experienced by the subject 12. For example, if the apnea-degree-sensor assembly 128 indicates that the degree to which a subject's airway 14 is open is below a target range, then the controller 134 is configured to control the pump assembly 118 or the pressure-regulator assembly 120 to change (e.g., increase) the magnitude of the negative pressure within at least one pressure region so as to increase the degree to which the subject's airway is open in an effort to drive the degree of airway openness into the target range—increasing the degree to which the subject's airway is open can mean, for example, increasing the cross-sectional area of the airway at the location at which it would otherwise become blocked. In contrast, if the apnea-degree-sensor assembly 128 indicates that the degree to which the subject's airway 14 is open is above the target range, then the controller 134 is configured to control the pump assembly 118 or the pressure-regulator assembly 120 to change (e.g., decrease) the magnitude of the negative pressure within at least one pressure region so as to decrease the degree to which the subject's airway is open in an effort to drive the degree of airway openness into the target range. That is, the pump assembly 118, the pressure-regulator assembly 120, the valve assembly 122, the apnea-degree-sensor assembly 128, and the controller 134 form at least part of a feedback loop for maintaining the degree to which the subject's airway 14 is open within a programmed, or otherwise set, target range so as to reduce (e.g., to zero) the degree of apnea experienced by the subject 12; alternatively, at least the controller 134 may be omitted from this feedback loop. The apnea-degree-sensor assembly 128 is further described below in conjunction with FIGS. 9-13.

The memory 130 can be any suitable type of volatile (e.g., DRAM, SRAM) or nonvolatile (e.g., EPROM, EEPROM, FLASH) memory, is configured to store program instructions that the controller 134 is configured to execute, and is configured to store other software, firmware, and data for the system 70. For example, the memory 130 can be configured to store one or more safety threshold levels, or other threshold levels, for each pressure chamber, to store one or more apnea-degree target ranges, and to store one more configuration or operation parameters for the negative-pressure sleep-apnea system 70 (FIGS. 4-7). Furthermore, the memory 130 can be configured to include a look-up table (LUT) 148, which is configured to correlate a signal level received from the apnea-degree-sensor assembly 128 with a degree of apnea (e.g., a degree to which the subject's airway 14 (FIG. 1) is open) as further described below in conjunction with FIG. 13; the memory can also be configured to store a representation of a curve that correlates the signal level from the apnea-degree-sensor assembly with a degree of sleep apnea.

The temperature-control assembly 132 is configured to control the respective temperature of the one or more pressure regions between the collar 76 (FIGS. 4-7) and the subject's neck 50 (FIG. 4), for example, for the comfort of the subject 12 (FIG. 4). The assembly 132 can be configured to be coupled to one or more heating elements (e.g., resistive heating elements) and cooling elements (e.g., thermoelectric cooling elements) that are strategically placed around the collar 76 (e.g., inside or on a surface of the collar), and can be configured to be coupled to one or more temperature sensors also so strategically placed; the heating elements, cooling elements, and temperature sensors may be included in the temperature-control assembly, or may be separate from the temperature-control assembly. In response to an indication (e.g., a temperature signal) from one such temperature sensor, the temperature-control assembly 132 can be configured to adjust the temperature in a corresponding pressure region to be within a programmed, or an otherwise set, temperature range. Alternatively, the assembly 132 can be configured to provide the respective indication of temperature for each pressure region to the controller 134, which can be configured to control the heating and cooling elements to maintain the temperature within each of the pressure regions within a respective temperature range. Furthermore, the temperature-control assembly 132 can be coupled to valves that are strategically placed around the collar 76 to vent the one or more pressure regions to the ambient air to help control the respective level of humidity, or the temperature, within each pressure chamber; these valves may form part of the temperature-control assembly or the valve assembly 122, or may be separate from these assemblies. Such valves are further described below in conjunction with FIGS. 14-22.

The controller 134 can include a processor, microprocessor, microcontroller, or any other suitable instruction-executing or non-instruction-executing computing machine, and is configured to control the components of the component module 74 as described above, and can also be configured to control one or more other components of the sleep-apnea system 70 (FIGS. 4-7) in general. The controller 134 can be configured to execute program instructions that are stored in the memory 130, and to use the memory as working memory when performing calculations or otherwise making determinations.

Furthermore, the controller 134 can be configured to change (e.g., reduce) the magnitude of the pressure within each of one or more pressure regions at a set time, or in response to an increase in ambient light (e.g., as an indication that it is morning), to assist the subject 12 (FIG. 4) in awakening, or to change (e.g., reduce) the pressure magnitude in response to an indication from the apnea-level-degree sensor assembly 128 that the subject is awakening.

For example, the controller 134 can be configured to begin changing the respective pressure within each of one or more pressure regions at a settable start time, and to control the one or more pressures according to a settable pressure profile for a settable duration that ends at a settable stop time, where the pressure profile can include changing the one or more pressures linearly, or otherwise monotonically, over the settable duration, and where the pressure profile may be common to the one or more pressure regions, or there may be multiple pressure profiles each associated with a respective group of the one or more pressure regions. Alternatively, instead of a settable stop time, the controller 134 may stop changing the one or more pressures individually when each of the one or more pressures exceeds a stop threshold, or may stop changing the one or more pressures at about the same time when any one of the one or more pressures exceeds the stop threshold. And, if after the duration of this wake-up procedure the controller 134 determines that the subject 12 (FIG. 4) is still asleep, then the controller can return to treating the subject's sleep apnea in the manner described above. Furthermore, although this wake-up procedure is described in conjunction with the system 70, which generates one or more negative pressures for treating sleep apnea, this wake-up procedure can be modified for a system, such as a CPAP system, that generates one or more positive pressures for treating sleep apnea. Moreover, the controller 134 can implement this procedure for a reason other than waking the subject 12.

Still referring to FIG. 8, alternate embodiments of the component module 74 are contemplated. For example, the module 74 may omit any one or more of the above-described components, or may include one or more other components. Furthermore, one or more of the above-described functions may be performed by one or more components other than the one or more components to which the operation is attributed. Moreover, at least the controller 134 may be implemented in software, firmware, hardware, or a combination or subcombination of any of software, firmware, and hardware.

Figure 9:
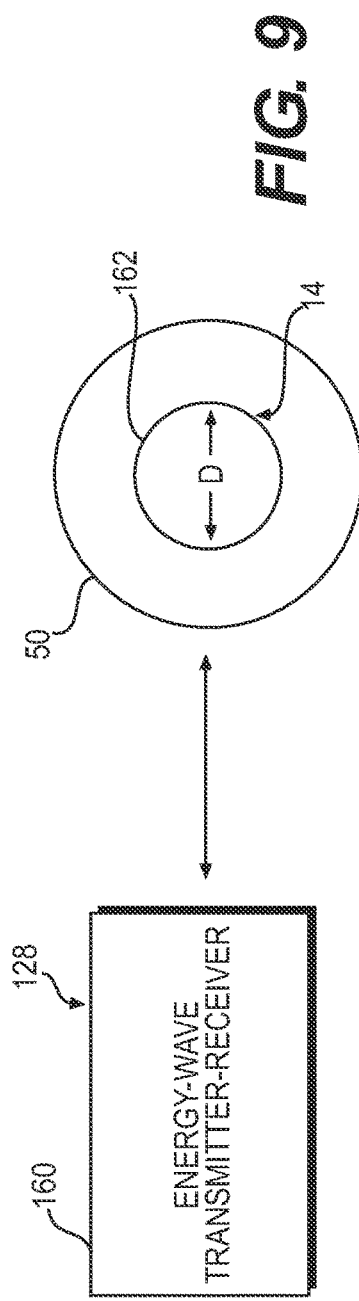
FIG. 9 is a diagram of a portion of the apnea-degree-sensor assembly of FIG. 8, and of a cross section of a neck and an airway of a subject, according to an embodiment.

FIG. 9 is a diagram of a portion of the apnea-degree-sensor assembly 128 of FIG. 8, and a cross section of the neck 50 (FIG. 4) and airway 14 (FIG. 1) of the subject 12 (FIG. 4), according to an embodiment; although the neck is shown as having an oval cross section and the airway is shown as having a circular cross section, the neck and airway may each have a respective other cross section.

The sensor assembly 128 includes an energy-wave transmitter-receiver 160, which is configured to transmit an energy wave toward the neck 50 and airway 14, to receive portions of the transmitted energy wave redirected (e.g., reflected) by regions of the surface 162 of a wall of the airway, and to determine the degree to which the airway is open in response to the received portions of the energy wave, or to provide information related to the received portions of the energy wave to the controller 134 so that the controller can determine the degree to which the airway is open. Alternatively, the sensor assembly 128 can determine the degree to which the airway 14 is collapsed, or provide information so that the controller 134 can determine the degree to which the airway is collapsed. For example, the sensor assembly 128, or the controller 134, can use the received redirected portions of the energy wave to determine a dimension D of the airway 14, with the value of D corresponding to the degree to which the airway is open (or collapsed). That is, the larger the value of D, the higher the degree to which the airway 14 is open (the lower the degree to which the airway is collapsed), and the smaller the value of D, the lower the degree to which the airway is open (the higher the degree to which the airway is collapsed)—hereinafter, only determining the degree to which the airway is open is described, it being understood that the corresponding description can also apply to determining the degree to which the airway is collapsed. Alternatively, the sensor assembly 128, or the controller 134, can use the received redirected portions of the energy wave to determine more than one dimension of the airway 14, or to acquire an image of the airway and to determine one or more airway dimensions from the acquired image.

The transmitter-receiver 160 can be configured to transmit any suitable type of energy wave that the surface 162 of the airway 14 at least partially redirects. For example, the transmitter-receiver 160 can be configured to transmit an acoustic ultrasound wave such as used in conventional ultrasound machines, or a micro-impulse-radar wave. Furthermore, the transmitter-receiver 160 can be configured to transmit a continuous energy wave, a pulsed energy wave, or any other suitable type of energy wave.

The transmitter-receiver 160 can include multiple transmitters and receivers so as to obtain an "image" of an entire cross section of the airway 14, or can include fewer, or one, transmitter that the sensor assembly 128 sweeps so as to cover an entire cross section of the airway, and fewer, or one, receiver that the sensor assembly sweeps in a similar manner, where the sensor assembly may sweep the transmitter or receiver mechanically or electronically (e.g., as in beam forming with a phased-array radar). If the transmitter-receiver 160 includes multiple transmitters or receivers, then these may be strategically located at various locations inside, or on a surface of, the collar 76 (FIGS. 4-7), or within the component module 74 (FIGS. 4-8). An example of a suitable transmitter and a suitable receiver includes a transducer, e.g., a piezoelectric transducer that can operate as a transmitter at one time and a receiver at another time.

The sensor assembly 128, or the controller 134, is configured to determine the dimension D of the airway 14 by analyzing one or more of the time delay (e.g., relative to the time of wave transmission), the phase (e.g., relative to the transmitted phase), the frequency spectrum (e.g., relative to the frequency spectrum of the transmitted wave), the wave shape (e.g., relative to the wave shape of the transmitted wave), the power (e.g., relative to the transmitted power), and the amplitude (e.g., relative to the amplitude of the transmitted wave) of each of one or more of the received redirected portions of the energy wave in any suitable manner, such as, for example, in the manner in which an ultrasound machine analyzes received redirected portions of transmitted acoustic waves that are redirected by internal tissues of a subject.

Figure 10:
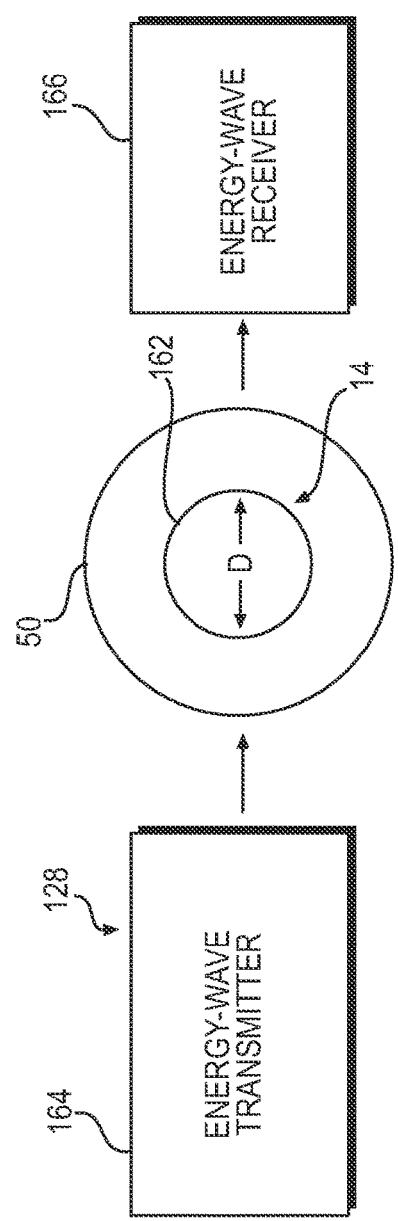
FIG. 10 is a diagram of a portion of the apnea-degree-sensor assembly of FIG. 8, and of a cross section of neck and an airway of a subject, according to another embodiment.

FIG. 10 is a diagram of a portion of the apnea-degree-sensor assembly 128 of FIG. 8, and a cross section of the neck 50 (FIG. 4) and airway 14 (FIG. 1) of the subject 12 (FIG. 4), according to another embodiment; although the neck is shown as having an oval cross section and the airway is shown as having a circular cross section, the neck and airway may each have a respective other cross section.

The sensor assembly 128 includes an energy-wave transmitter 164, which is configured to transmit an energy wave toward the airway 14, and an energy-wave receiver 166, which is configured to receive one or more portions of the transmitted energy wave that penetrate the neck 50 and airway 14, and is configured to determine the degree to which the airway is open in response to the received portions of the energy wave, or to provide information related to the received portions of the energy wave to the controller 134 so that the controller can determine the degree to which the airway is open. For example, the sensor assembly 128, or the controller 134, can use the received portions of the energy wave to determine a dimension D of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the received portions of the energy wave to determine more than one dimension of the airway 14.

The transmitter 164 can be configured to transmit any suitable type of energy wave that can pass, at least partially, through a first portion the neck 50 between the transmitter and the airway 14, through the airway, and through a second portion of the neck between the airway and the receiver 166. For example, the transmitter 164 can be configured to transmit an x-ray wave such as used in conventional x-ray machines, or a micro-impulse-radar wave. Furthermore, the transmitter 134 can be configured to transmit a continuous energy wave, a pulsed energy wave, or any other suitable type of energy wave.

The transmitter 164 can include multiple transmitters, and the receiver 166 can include multiple receivers, so that the sensor assembly 128 can obtain an "image" of an entire cross section of the airway 14. Or the transmitter 164 can include fewer, or one, transmitter that the sensor assembly 128 sweeps so as to cover an entire cross section of the airway 14, and the receiver 166 can include fewer, or one, receiver that the sensor assembly sweeps in a similar manner, where the sensor assembly may sweep the transmitter or receiver mechanically or electronically (e.g., as in beam forming with a phased-array radar). If the transmitter 164 includes multiple transmitters, or the receiver 166 includes multiple receivers, then these may be strategically located at various locations inside, or on a surface of, the collar 76 (FIGS. 4-7), or within the component module 74 (FIGS. 4-8).

The sensor assembly 128, or the controller 134, is configured to determine the dimension D by analyzing one or more of the time delay (e.g., relative to the time of wave transmission), the phase (e.g., relative to the transmitted phase), the frequency spectrum (e.g., relative to the frequency spectrum of the transmitted wave), the wave shape (e.g., relative to the wave shape of the transmitted wave), the power (e.g., relative to the transmitted power), and the amplitude (e.g., relative to the amplitude of the transmitted wave), of each of one or more of the received portions of the energy wave in any suitable manner, such as, for example, in the manner in which an x-ray machine analyzes received portions of transmitted x-ray waves.

Figure 11:
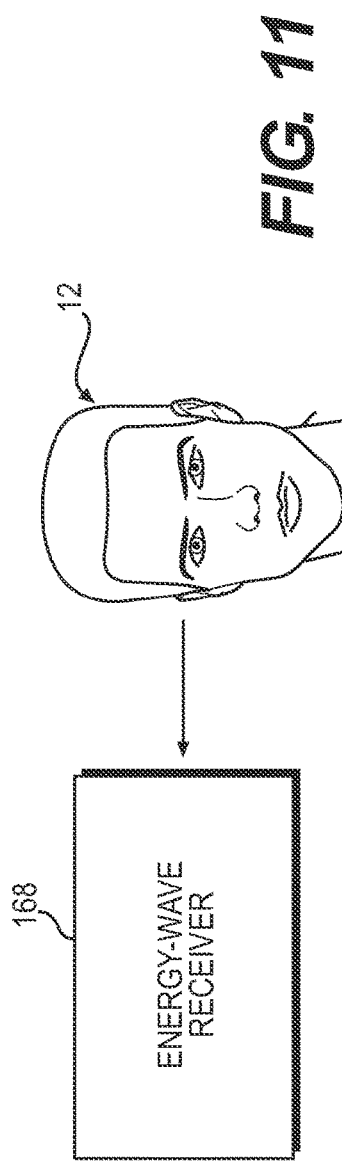
FIG. 11 is a diagram of a portion of the apnea-degree-sensor assembly of FIG. 8, and of a cross section of a neck and an airway of a subject, according to yet another embodiment.

FIG. 11 is a diagram of a portion of the apnea-degree-sensor assembly 128 of FIG. 8, and of the subject 12 of FIG. 4, according to yet another embodiment.

The sensor assembly 128 includes an energy-wave receiver 168, which is configured to receive one or more portions of one or more energy waves generated by the subject 12, and is configured to determine the degree to which the subject's airway 14 (FIGS. 9-10) is open in response to the received one or more energy-wave portions, or to provide information related to the received one or more energy-wave portions to the controller 134 so that the controller can determine the degree to which the airway is open. For example, the sensor assembly 128, or the controller 134, can use the received one or more energy-wave portions to determine a dimension D (FIGS. 9-10) of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the received one or more energy-wave portions to determine more than one dimension of the airway 14.

The energy-wave receiver 168 can be configured to receive any suitable type of energy wave that the subject 12 generates. For example, the receiver 168 can be configured to receive an acoustic wave, such as generated when the subject 12 makes respiratory sounds (e.g., breathing or snoring sounds), a disturbance in a light wave, such as generated when the subject moves his eyes (even when the eyes are closed) or another body part (e.g., nose, mouth, jaw, or chin), or an electromagnetic wave such as a brain wave or a heart wave (e.g., an electrocardiogram wave).

The sensor assembly 128 can include multiple receivers 168 so as to be able to pick up energy waves emanating from anywhere around the head region, neck region, or other region of the subject 12, or can include fewer, or one, receiver that the sensor assembly sweeps mechanically or electronically (e.g., as in beam forming with a phased-array radar). If the sensor assembly 128 includes multiple receivers 168, then these may be strategically located at various locations inside, or on a surface of, the collar 76 (FIG. 4), or within the component module 74 (FIGS. 4-8). Furthermore, the one or more receivers 168 may be directed at regions (e.g., head, chest) of the subject other than the subject's neck.

The sensor assembly 128, or the controller 134, is configured to determine the dimension D by analyzing one or more of the phase, the frequency spectrum, the wave shape, the power, and the amplitude of each of one or more of the received energy-wave portions in a conventional manner, and then correlating the results of this analysis with a degree to which the airway 14 (FIGS. 9-10) is open using, for example, the look-up table 148 of FIG. 8 or a fitted curve. A procedure for developing and using such a correlation is described below in conjunction with FIG. 13.

FIG. 12 is a diagram of a portion of the apnea-degree-sensor assembly 128 of FIG. 8, and of the subject 12 of FIG. 4, according to still another embodiment.

The sensor assembly 128 includes a biological-condition sensor 170, which is configured to sense one or more biological conditions of the subject 12, and is configured to determine the degree to which the subject's airway 14 (FIGS. 9-10) is open in response to the one or more sensed biological conditions, or to provide information related to the sensed one or more biological conditions to the controller 134 so that the controller can determine the degree to which the airway is open. For example, the sensor assembly 128, or the controller 134, can use the sensed one or more biological conditions to determine a dimension D (FIGS. 9-10) of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the sensed one or more biological conditions to determine more than one dimension of the airway 14.

The sensor 170 can be configured to sense any suitable type of biological condition of the subject 12. Examples of such a biological condition include respiratory rate, heart rate, blood-glucose level, blood-oxygen level, blood-adrenaline level, body temperature, body-perspiration level, body-movement level (e.g., the sensor can include an accelerometer), blood pressure, expiration-gas composition, and body-part position (e.g., chin position, the degree to which the subject's mouth is open, or the degree to which the subject's nostrils are flared).

The sensor assembly 128 can include multiple biological-condition sensors 170 so as to be able to sense multiple biological conditions of the subject 12, and the one or more sensors may be strategically located at various locations inside, or on a surface of, the collar 76 (FIGS. 4-7), within the component module 74 (FIGS. 4-8), or even on or in the subject's body, in which case each such sensor can be tethered to the component module 74 (FIGS. 4-8) with a wire or other suitable connector, or can communicate with a base portion of the sensor assembly 128 wirelessly. For example, the sensor assembly 128 can utilize one or more motion sensors configured to monitor motion of the sleeping subject 12. These one or more sensors can be on-board the collar assembly 72 (e.g., one or more accelerometers), or can be remote from the collar assembly (e.g., accelerometers attached to the limbs or torso of the subject, or remote imagers, e.g., low-light or IR cameras, or micro-impulse radar). A sensor that is remote from the collar assembly 72 can deliver its measurements to a portion of the sensor assembly 128 that is on-board the collar assembly wirelessly or via one or more signal cables. In response to readings provided by such one or more sensors, the controller 134 can interpret excessive motion (e.g., thrashing, or frequent posture changes) or lack of motion (e.g., excessive stillness) of the subject 12 as an indication that the subject is experiencing sleep apnea.

The sensor assembly 128, or the controller 134, is configured to determine the dimension D by analyzing one or more parameters of each of one or more of the sensed biological conditions in any suitable manner, and then correlating the results of this analysis with a degree to which the airway 14 (FIGS. 9-10) is open using, for example, the look-up table 148 of FIG. 8, or a fitted curve stored in the memory 130. A procedure for developing and using such a correlation is described below in conjunction with FIG. 13.

Referring to FIGS. 8-12, alternate embodiments of the apnea-degree-sensor assembly 128 are contemplated. For example, the sensor assembly 128 can include any combination or sub-combination of one or more of each of the energy-wave transmitter-receiver 160, the energy-wave transmitter 164, the energy-wave receivers 166 and 168, and the biological-condition sensor 170.

FIG. 13 is a flow diagram 180 of a procedure for correlating one or more biological conditions of the subject 12 (e.g., FIG. 12) to a degree of sleep apnea that the subject is experiencing, according to an embodiment. For example, the procedure may correlate the one or more biological conditions to a degree to which the subject's airway 14 (e.g., FIGS. 9-10) is open, the degree of airway openness being related to the degree of sleep apnea that the subject is experiencing. In the example described below in conjunction with the flow diagram 180, the correlated biological condition is the respiratory rate of the subject 12, although it is understood that any one or more other biological conditions sensed by any of the embodiments of the apnea-degree-sensor assembly 128 described above in conjunction with FIGS. 8-12 can be correlated in a similar manner. Furthermore, a sleep doctor or sleep technician can perform the correlation with the subject 12 in sleep-laboratory setting, and then, for example, program the look-up-table (LUT) 148 (FIG. 8) of the subject's sleep-apnea-treatment system 70 with a correlation-data structure, or program the memory 130 (FIG. 8) of the system with a representation of a fitted curve that relates the biological condition to the degree of sleep apnea. Alternatively, the subject's system 70, or a laboratory version of the system, may perform this procedure with or without the assistance of a sleep-medicine professional or the subject 12.

At a step 182, one, e.g., a sleep technician, monitors a degree to which the airway 14 (FIGS. 9-10) of the subject 12 (FIG. 4) is open while the subject is sleeping. For example, one may use ultrasound to monitor one or more dimensions D (FIGS. 9-10) of the airway 14 as described above in conjunction with FIG. 9. The ultrasound waves and resulting ultrasound images may be generated by an embodiment of the apnea-treatment system 70 described above in conjunction with FIG. 9, or may be generated by an independent ultrasound machine.

Simultaneously at a step 184, one also monitors one or more biological conditions of the subject 12 (FIG. 4) that are related to the degree to which the subject's airway 14 (FIGS. 9-10) is open while the subject is sleeping. For example, one may monitor the volume or frequency spectrum of the subject's respiratory sounds (e.g., breathing, snoring), or, as in this example, the subject's respiratory rate.

Then, after performing steps 182 and 184 for a suitable period of time (e.g., 2-8 hours while the subject is sleeping), at a step 186, one correlates each of the monitored one or more biological conditions to the degree of openness of the airway 14 (FIGS. 9-10). For example, one may digitize the observed values of the subject's respiratory rate at corresponding sample times, digitize the observed values of the degrees of openness of the subject's airway 14 at the same corresponding sample times, and match each value of the respiratory rate taken at a respective sample time with the corresponding degree of airway openness taken at the same respective sample time. Furthermore, in some cases, a predictive correlation can be derived. For example, it may be determined that during a period (e.g., two-minutes long) preceding an apnea-inducing closure of the airway 14 of the subject 12, a particular pattern of respiratory sounds often precedes the airway closure. Therefore, such a correlation can be used to preemptively apply negative pressure to a selected one or more regions of the subject's neck 50 to prevent the onset of a sleep-apnea event before it even occurs.

Next, at a step 188, one generates a respective data structure that represents the correlation between each of the biological conditions to the degree of airway openness.

For example, on may generate a data structure that represents the correlation of the digitized values of the respiratory rate with the corresponding digitized values of the degree of airway openness, and store this data structure in the LUT 148 (FIG. 8). That is, one may associate each of the values of the respiratory rate with a corresponding address of the LUT 148, and, at each address, store the degree of airway openness corresponding to the value of the respiratory rate associated with the address.

When the apnea-degree-sensor assembly 128 (FIGS. 8 and 12) provides a digitized value of the subject's respiratory rate, a respiratory-rate-value-to-address converter (such a converter can be part of the assembly 128, can be part of any other component of the component module 74, or can be a separate component of the component module) converts the value into an address of the LUT 148. And the sensor assembly 128, or the controller 134, obtains the corresponding value of the degree of airway openness from the location of the LUT 148 at this address, and uses this value of the degree of airway openness to control the pump assembly 118 (FIG. 8), pressure-regulator assembly 120, or valve assembly 122 so as to control the level of sleep apnea experienced by the subject 12. For example, if the value of the degree of airway openness obtained from the LUT 148 is below a programmed, or otherwise set, apnea-level target range, then the sensor assembly 128 or controller 134 can act to increase the degree of airway openness toward the target range; in contrast, if the value of the degree of airway openness obtained from the LUT is above the apnea-level target range, then the sensor assembly 128 or controller 134 can act to decrease the degree of airway openness toward the target range.

Alternatively, one may fit the digitized values of the respiratory rate and the corresponding digitized values of the degree of airway openness to a curve, and store a representation of this curve in the memory 130 (FIG. 8).

When the apnea-degree-sensor assembly 128 (FIGS. 8 and 12) provides a digitized value of the subject's respiratory rate, the controller 134 converts the value into a corresponding value of the degree of airway openness using the representation of the fitted curve, and uses this value of the degree of airway openness to control the pump assembly 118 (FIG. 8), pressure-regulator assembly 120, or valve assembly 122 so as to control the level of sleep apnea experienced by the subject 12. For example, if the fitted curve is a straight line, then the mathematical expression defining the line in terms of the respiratory-rate values and the degree-of-airway-openness values is stored in the memory 130, and the controller 134 uses this mathematical expression to calculate the degree of airway openness that corresponds to the provided value of the respiratory rate. So, if the value of the degree of airway openness obtained from the fitted curve is below a programmed, or otherwise set, apnea-level target range, then the sensor assembly 128 or controller 134 can act to increase the degree of airway openness toward the target range; in contrast, if the value of the degree of airway openness obtained from the fitted curve is above the apnea-level target range, then the sensor assembly 128 or controller 134 can act to decrease the degree of airway openness toward the target range.

Still referring to FIG. 13, alternate embodiments of the procedure represented by the flow diagram 180 are contemplated. For example, any one or more of the recited steps 182-188 may be omitted, and one or more other steps may be added. Furthermore, any of the recited steps may be performed manually, by a computing apparatus, or by any other suitable apparatus.

Figure 14:
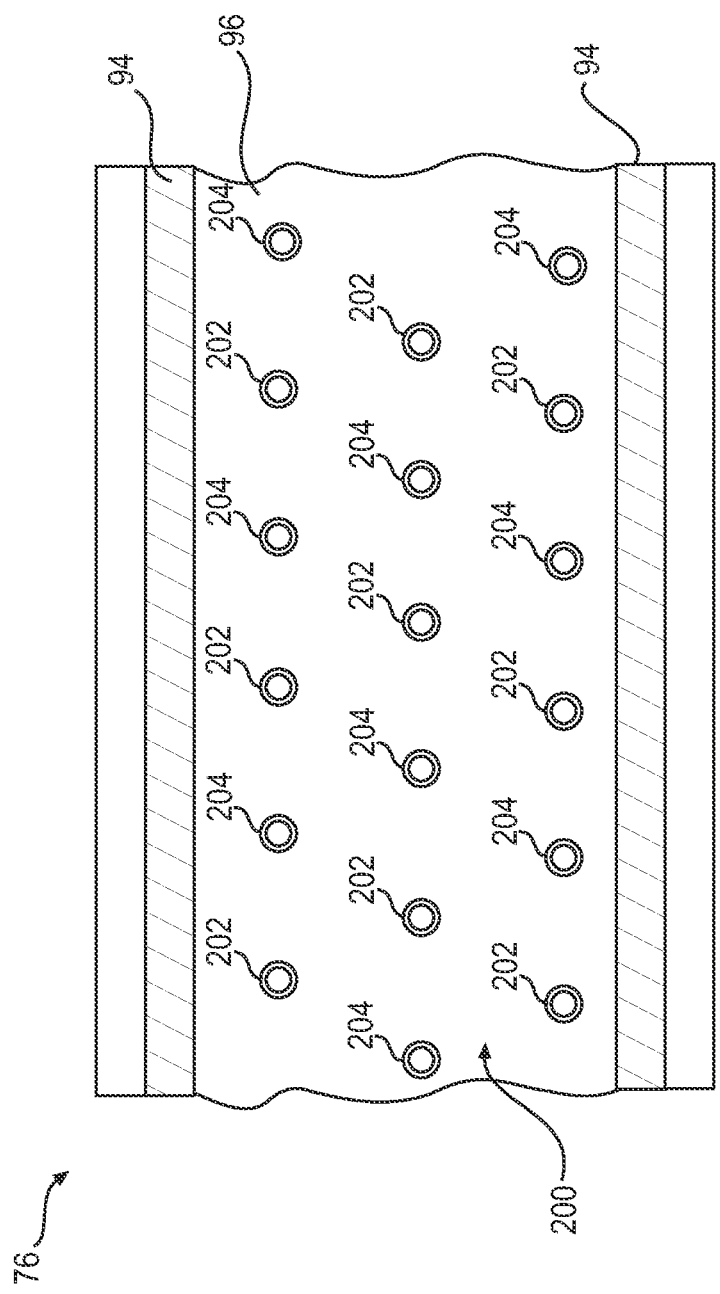
FIG. 14 is a diagram of sealing and vacuum surfaces of the collars of FIGS. 4-7, according to an embodiment.

FIG. 14 is a plan view of an inner portion of the collar 76 of FIGS. 4-7, including portions of two sealing surfaces 94 and a portion of vacuum surface 96, according to an embodiment. "Inner portion" means a portion of the collar 76 that is configured to face the neck 50 (FIG. 4) of the subject 12 (FIG. 4) while the subject is wearing the sleep-apnea-treatment system 70 (FIGS. 4-7).

The sealing surfaces 94 are each configured to contact a respective portion of the neck 50 (FIG. 4) of the subject 12 (FIG. 4), and to form a respective airtight seal with the respective contacted neck portion.

And the vacuum surface 96 is configured to form a negative-pressure region 200 together with the sealing surfaces 94, the contacted portions of the neck 50, and the portion of the subject's neck opposite the vacuum surface—the vacuum surface may also be called a pressure surface, and the negative-pressure region may also be called a vacuum region, pressure chamber, or vacuum chamber. As described below in conjunction with FIGS. 16-22, the collar 76 can include a frame such that at least a portion of the vacuum surface 96 does not contact the subject's neck 50.

Each sealing surface 94 can be rigid, semi-rigid, or flexible, and may be formed from any suitable sealing material, such as plastic, rubber, or silicone.

The vacuum surface 96 also can be rigid, semi-rigid, or flexible, can be formed from any suitable material, such as plastic, rubber, or silicone, and includes a set of one or more inlet openings 202, and a set of one or more outlet openings 204; the inlet and outlet openings can be arranged relative to each other in any suitable pattern, and can have any suitable sizes and shapes. Furthermore, nozzles, one-way valves, or other suitable components may be disposed within one or more of the openings 202 and 204.

The one or more inlet openings 202 are configured to allow air to flow from an outer portion of the collar 76, through one or more inlet valves (described below in conjunction with FIGS. 16-22), through the one or more inlet openings, and into the negative-pressure region 200—"outer portion" means a portion of the collar 76 that is configured to face away from the neck 50 (FIG. 4) of the subject 12 (FIG. 4) while the subject is wearing the sleep-apnea-treatment system 70 (FIGS. 4-7). Hoses and couplings within the collar 76 can couple the one or more inlet openings 202 to the one or more inlet valves. Furthermore, some or all of these hoses and couplings, the one or more inlet valves, and the one or more inlet openings 202 can be considered to be part of the valve assembly 122 (FIG. 8).

And the one or more outlet openings 204 are configured to allow air to flow from the negative-pressure region 200, through the one or more outlet openings, through the valve assembly 122 (FIG. 8) and the pressure-regulator assembly 120 (FIG. 8), through the pump assembly 118 (FIG. 8), and out through the outlet valve 102 (FIGS. 4-8). Hoses and couplings within the collar 76 can couple the one or more outlet openings 204 to the valve and pressure-regulator assemblies 120 and 122 (FIG. 8). Furthermore, some or all of these hoses and couplings and the one or more outlet openings 204 can be considered to be part of the valve assembly 122 (FIG. 8).

Allowing air to flow through the negative-pressure region 200 may be more comfortable for the subject 12 (FIG. 4) than if no inlet openings 202 were present, because without one or more inlet openings, the air within the pressure region could become hot or humid due to the subject perspiring, and could become otherwise "stale." Even though the negative-pressure sleep-apnea treatment system 70 (FIGS. 4-7) can include the temperature-control assembly 132 (FIG. 8) to cool the air within the pressure region 200, the above-described airflow can reduce or eliminate the need for such cooling, and, therefore, can reduce the energy that the system consumes, and can allow one to reduce the cost of the system by omitting the cooling capability from the temperature-control assembly.

Still referring to FIG. 14, alternate embodiments of the sealing surfaces 94 and vacuum surface 96 are contemplated. For example, although shown arranged parallel to one another, the sealing surfaces 96 can be arranged with any other suitable orientation relative to one another. Furthermore, the collar 76 can include fewer or more than two sealing surfaces 94, and more than one vacuum surface 96. Moreover, one or more of the sealing surfaces 94 can each include one or more outlet openings 204 to increase the strength of the seal that the respective surfaces make with the neck 50 (FIG. 4). In addition, one or more portions of a sealing surface 94 and one or more portions of a vacuum surface 96 can be parts of a same surface. Furthermore, the portion of the vacuum surface 96 that forms a respective pressure region 200 can be fully or partially surrounded by one or more sealing surfaces 96 (if partially surrounded, then part of the vacuum surface can form the remainder of the seal around the pressure region by forming an airtight seal with a portion of the subject's neck 50 (FIG. 4) opposite the sealing portion of the vacuum surface. Moreover, the airtight seal that the one or more sealing surfaces 94 and one or more vacuum surfaces 96 form with respective portions of the subject's neck 50 (FIG. 4) to form a pressure region 200 can extend only partially around the pressure region; this can, for example, eliminate the need for the inlet openings 202, because the pump assembly 118 (FIG. 8) can draw in outside air through a side of the pressure region where no airtight seal is formed. In addition, one or more sealing surfaces 94 can each include one or more outlet openings 204, which enable each sealing surface to use negative pressure to form a seal against the skin of the subject. The one or more sealing surfaces 94 can each include an array of closely spaced discrete outlet openings 204, or can include a porous surface. The openings 204 or pores in the one or more sealing surfaces can be coupled through a manifold or plenum to a pump (e.g., belonging to the pump assembly 118, pressure-regulator assembly 120, or valve assembly 122), which is used to provide the negative pressure causing the sealing surface to adhere to the skin of the user. The one or more negative-pressure levels that form the one or more seals can be different from the one or more negative-pressure levels in the one or more pressure regions 200. Alternatively, the pressure level used to form a seal and the pressure level in an adjacent pressure region 200 can be the same; for example, a manifold servicing the openings/pores of a sealing surface 94 can couple to the adjacent pressure region between, thereby not requiring a separate pump.

FIG. 15 is a plan view of a portion of a sealing surface 94, according to an embodiment.

The portion of the sealing surface 94 of FIG. 15 can be similar to the portions of the sealing surfaces 94 of FIG. 14, except that the portion of the sealing surface of FIG. 15 includes one or more sealant-dispensing openings 210.

Each sealant-dispensing opening 210 is configured to eject a sealant from the sealant-dispersing assembly 124 of FIG. 8, where the sealant is configured to fortify, or repair a leak in, the airtight seal that the sealing surface 94 is configured to form with a portion of the neck 50 (FIG. 4) of the subject 12 (FIG. 4) as described above in conjunction with FIG. 14. For example, the sealant may repair a leak formed around one or more strands of the subject's hair that lay between the sealing surface 94 and the subject's neck 50 (FIG. 4). Furthermore, nozzles, one-way valves, or other suitable components may be disposed within one or more of the openings 210. Moreover, hoses and couplings within the collar 76 (FIG. 14) can couple the one or more sealant-dispensing openings 210 to the sealant-dispenser assembly 124 (FIG. 8); some or all of these hoses and couplings, and the one or more sealant-dispensing openings, can be considered to be part of the sealant-dispenser assembly. In addition, the one or more sealant-dispensing openings 210 can have any suitable sizes, shapes, and can be located at any suitable spacing and in any suitable pattern along the sealing surface 94. Furthermore, an opening 210 can overlap an edge 212 of the sealing surface 94 such that one portion of the sealant-dispensing opening is formed in the sealing surface, and another portion is formed in the adjacent vacuum surface 96 (FIG. 14). Or, an opening 210 can be formed entirely in the vacuum surface 96, for example, near an edge 212 of the sealing surface 94.

In operation of the sleep-apnea system 70 (FIGS. 4-7), according to an embodiment, if, for example, the controller 134 (FIG. 8) detects a leak in a pressure region 200 (FIG. 14), then the controller can cause the sealant-dispenser assembly 124 (FIG. 8) to dispense a sealant from the reservoir 146 (FIG. 8) via one or more of the sealant-dispensing openings 210 along a portion of a sealing surface 94 that forms, or otherwise borders, the pressure region. For example, the controller 134 can cause the sealant-dispenser assembly 124 to dispense sealant from one opening 210 in the sealing surface 94 at a time until the controller detects that the leak has been sealed.

Still referring to FIG. 15, alternate embodiments are contemplated. For example, although only one sealing surface 94 is described, multiple sealing surfaces can include one or more sealant-dispensing openings 210. Furthermore, the sealant-dispenser assembly 124 (FIG. 8) can be configured to selectively dispense a sealant from one or more, but not all, of the sealant-dispensing openings 210 at any one time. Moreover, if an opening 210 includes a nozzle, then the sealant-dispenser assembly 124 may be able to orient the nozzle in a selected direction before, while, or after dispensing the sealant.

FIG. 16 is a view of a portion 220 of the collar 76 of FIGS. 4-7 and 14, according to an embodiment.

FIG. 17 is a cross-sectional view of a mid region of the collar portion 220 of FIG. 16 taken along a line A-A of FIG. 16, and of a portion 222 of a subject's neck 50 and airway 14, according to an embodiment.

Figure 18:
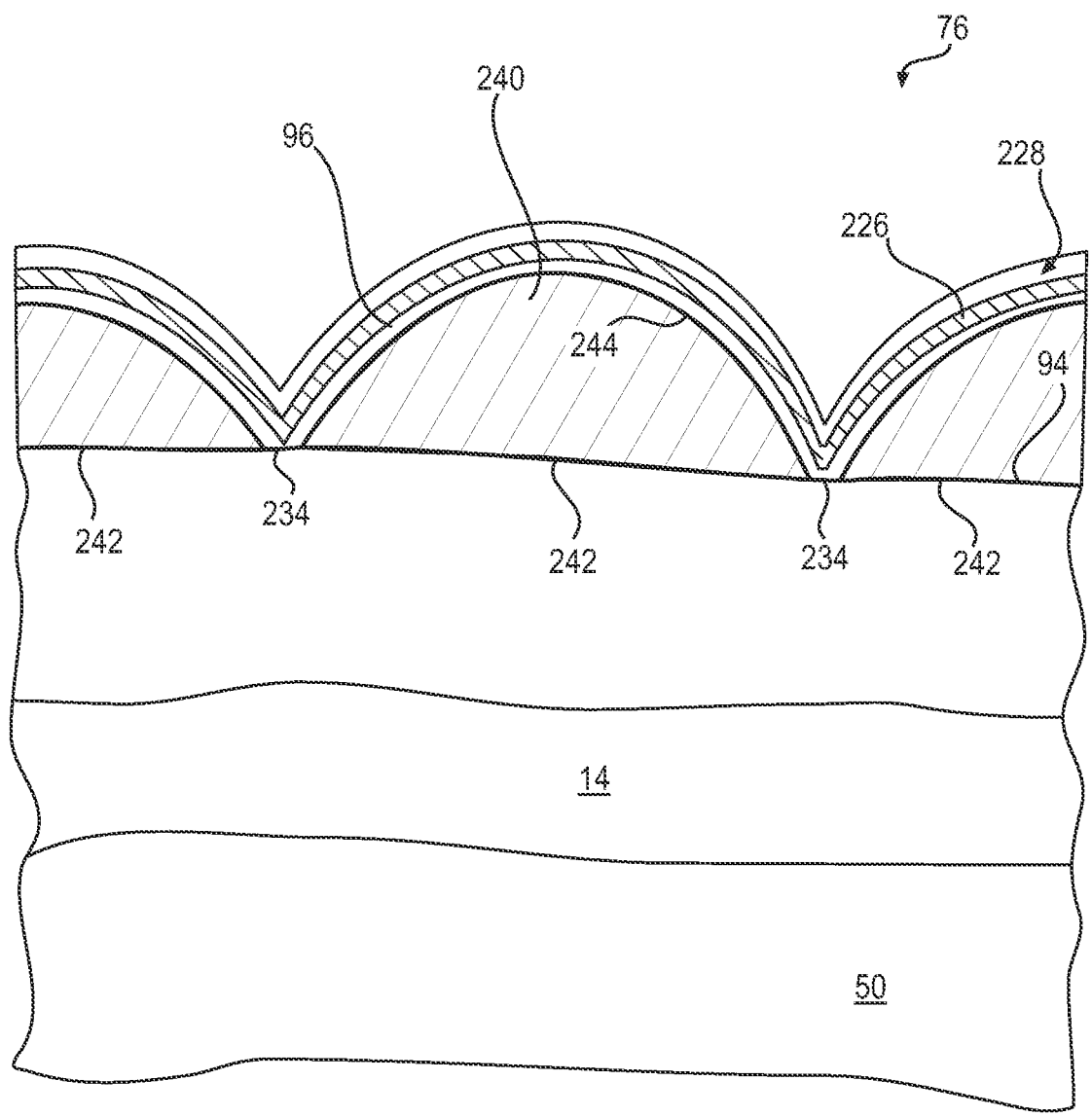
FIG. 18 is a view of an end region of the collar portion of FIG. 16, according to an embodiment.

FIG. 18 is a cross-sectional view of an end region of the collar portion 220 of FIG. 16, and of the portion 222 of the subject's neck 50 and airway 14, according to an embodiment.

Referring to FIGS. 16-17, the collar 76 includes one or more segments 224, which, while the negative-pressure sleep-apnea-treatment system 70 (FIGS. 4-7) is being worn by the subject 12 (FIG. 4), are configured to be oriented approximately in a circumferential direction around the subject's neck 50.

Each segment 224 is formed by a respective rigid, or semi-rigid, portion 226 of a frame 228. Each frame portion 226 has a curved shape, and can be made from any suitable material such as a plastic, a metal, or a wire mesh.

To each frame portion 226 is attached a respective portion of the vacuum surface 96 (described above in conjunction with, e.g., FIG. 14), and a respective portion of an outer covering 230, which can be made from any suitable material such as a plastic or a cloth. Any suitable attachment technique, such as cementing or gluing, may be used to attach the vacuum surface 96 and outer covering 230 to the frame portions 226.

Each frame portion 226 is attached to an adjacent frame portion at a respective joint 232 by any suitable attachment technique such as welding, bonding, cementing, or gluing. Alternatively, the frame 228 may be made from one piece such that the frame portions 226 are integral with one another. Or, the joints 232 may be flexibly coupled together, e.g., with hinges.

A respective sealing surface 94 (described above in conjunction with FIGS. 14-15) is disposed along each joint 232.

While the collar 76 is being worn by the subject 12 (FIG. 4), the sealing surfaces 94 engage respective portions 234 of the subject's neck 50 so as to form the pressure regions 200, one pressure region per collar segment 224 in this example.

Each collar segment 224 also includes a respective inlet valve 238, which allows the pump assembly 118 (FIG. 8) to draw outside air into the respective pressure regions 200 as described above in conjunction with FIG. 14.

Any hoses or couplings that may be disposed in the collar 76, for example as described above in conjunction with FIGS. 8 and 14-15, are omitted from FIGS. 16-18 for clarity.

Referring to FIG. 18, the cross section of an end region of the collar 76 is similar to the cross section of the mid region of the collar as described above in conjunction with FIG. 17, but with the addition of segment terminators 240.

The terminators 240 are configured to form airtight seals at the ends of the collar segments 224, and may be made from any suitable rigid or semi-rigid material such as plastic, metal, or wire mesh.

The sealing surfaces 94 extend along the bottoms of the terminators 240 and are configured to make airtight seals with portions 242 of the neck 50, and the curved tops of the terminators are attached to the vacuum surfaces 96 along seams 244 in any suitable airtight manner.

Alternately, the terminators 240 may be attached directly to the respective frame portions 226, or may be formed integrally with the frame portions or as an integral part of the frame 228 as a whole.

Referring to FIGS. 16-18, in operation of the sleep-apnea-treatment system 70 (FIGS. 4-7), according to an embodiment, the pump assembly 118 (FIG. 8) is configured to cause a negative pressure to exist within the negative-pressure regions 200 by drawing air from these regions; although the inlet valves 238 allow a flow of air into the negative-pressure regions, the power of the pump assembly overcomes this airflow to create the negative pressures within the negative-pressure regions. Furthermore, the negative pressures within the regions 200 may be the same or different from one another.

Because the pressure outside of the collar 76 is greater than the pressure within the pressure regions 200, the outside air effectively presses against the frame 228, which in turn presses the sealing surfaces 94 against the neck portions 234 and 242 to form respective airtight seals. Or, viewed another way, the frame 228 is effectively "sucked" against the neck 50 such that the sealing surfaces 94 are forced against the respective neck portions 234 and 242. This effect can be used as the primary mechanism for attaching the collar assembly 72 to the neck 50 of the subject 12, thus enabling a collar assembly that does not need to be positively attached to the subject via straps or by fully encircling the neck. Such a collar assembly 72 can generically utilize, in one or more of the pressure regions 200, a modest "gripping" level of negative pressure that is sufficient to hold the collar assembly against the subject's neck 50, but that is too weak to appreciably open his/her airway 14; and the collar assembly can increase the magnitude of the negative pressure in one or more of the pressure regions as needed to open the subject's airway 14, or to maintain the airway open, so as to arrest an apnea, or to prevent an apnea from occurring.

Furthermore, because the frame 228 and terminators 240 are rigid or semi-rigid, the frame portions 226 and the terminators hold the vacuum surfaces 96 away from the portions 246 of the neck 50 covered by the frame portions. Therefore, the negative pressure within the regions 200 can cause the neck portions 246 to expand outward, thus giving the desired result of "pulling" open the subject's airway 14. If the frame portions 226 and terminators 240 were not rigid or semi-rigid, then the vacuum surfaces 96 would collapse against the neck portions 246 such that the subject's airway 14 would not be "pulled" open as intended.

Still referring to FIGS. 16-18, in operation of the sleep-apnea-treatment system 70 (FIGS. 4-7), according to another embodiment, the system may regulate the pressures within the pressure regions 200 in a manner that mimics peristalsis.

For example, the system 70 can so regulate the pressures to reduce or eliminate the chances that the system will cause a portion 246 of the neck 50 to form an edema (e.g., a "hickey") caused by a prolonged continuous exposure to a negative pressure.

Peristalsis is a radially symmetrical contraction and relaxation of muscles that form a muscular tube, which contraction propagates in a wave down the muscular tube in an anterograde fashion. An example of such a muscular tube in humans is the esophagus, the muscles of which contract in a peristalsis manner to move food and drink from the mouth to the stomach.

In an embodiment, the pressure-regulator assembly 120 (FIG. 8) first increases the pressure (i.e., lessens the magnitude of the negative pressure) within the bottom pressure region 200 of the collar 76 while maintaining the pressures in the middle and top pressure regions unchanged. The amount and profile by which the pressure-regulator assembly 120 increases the pressure in the bottom pressure region 200, and the duration of this pressure increase, can be suitable to reduce or eliminate the chances of an edema forming in the bottom neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the bottom pressure region 200 until it reaches the level that the controller 134 (FIG. 8) determines is suitable to treat the subject's sleep apnea. The profile by which the pressure-regulator assembly 120 reduces the pressure within the bottom pressure region 200, and the duration of this pressure reduction, can be suitable to reduce or eliminate the chances of an edema forming in the bottom neck portion 246.

Then, while or after reducing the pressure in the bottom negative-pressure region 200, the pressure-regulator assembly 120 (FIG. 8) increases the pressure (i.e., lessens the magnitude of the negative pressure) within the middle pressure region 200 while maintaining the pressure in at least the top pressure region unchanged. The amount and profile by which the pressure-regulator assembly 120 increases the pressure within the middle pressure region 200, and the duration of this pressure increase, can be suitable to reduce or eliminate the chances of an edema forming in the middle neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the middle pressure region 200 until it reaches the level that the controller 134 (FIG. 8) determines is suitable to treat the subject's sleep apnea. The profile by which the pressure-regulator assembly 120 reduces the pressure in the middle pressure region 200, and the duration of this pressure reduction, may be suitable to reduce or eliminate the chances of an edema forming in the middle neck portion 246.

Then, while or after reducing the pressure in the middle negative-pressure region 200, the pressure-regulator assembly 120 (FIG. 8) increases the pressure (i.e., lessens the magnitude of the negative pressure) within the top pressure region 200 while maintaining the pressure in at least the bottom pressure region unchanged. The amount and profile by which the pressure-regulator assembly 120 increases the pressure within the top pressure region 200, and the duration of this pressure increase, can be suitable to reduce or eliminate the chances of an edema forming in the top neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the top pressure region 200 until it reaches the level that the controller 134 (FIG. 8) determines is suitable to treat the subject's sleep apnea. The profile by which the pressure-regulator assembly 120 reduces the pressure within the top pressure region 200, and the duration of this pressure reduction, may be suitable to reduce or eliminate the chances of an edema forming in the top neck portion 246.

In summary of the above-described peristalsis procedure, the controller 134 changes the pressures within the bottom, middle, and top pressure regions so that these pressures are offset from each other in time, and, therefore, in phase, and so that the controller effectively generates a pressure "wave" that propagates up or down the collar 76.

The controller 134 (FIG. 8) may perform this peristalsis procedure periodically at a programmed, or otherwise set, interval, or may do so in response to a sensor of the system 70 indicating that an edema of a threshold size has formed, or may soon form, in a region (e.g., a region 246) of the subject's neck 50. Furthermore, the controller 134 can cause one or more of the pressure regions 200 to have a respective positive pressure during respective portions of the peristalsis procedure, as long as the number of pressure regions having positive pressures at any one time is small enough so as not to cause the collar 76 to fully disengage from the subject's neck 50 (FIG. 4) or to otherwise cause a problem with the treatment of the subject's sleep apnea. For example, the controller 134 can be configured so that no more than one end pressure region (e.g., the top or the bottom pressure region) 200 has a reduced-magnitude negative pressure, or a positive pressure, at any one time.

Still referring to FIGS. 16-18, alternate embodiments of the collar 76, and of the system 70 (FIGS. 4-7) in general, are contemplated. For example, the collar segments 224 can have different sizes or shapes from one another and from what is described. Furthermore, there can be fewer or more than three segments 224. Moreover, the peristalsis action can propagate from top to bottom of the collar 76 instead of from bottom to top, can alternate propagation directions, and can be altered in any suitable manner.

Figure 19:
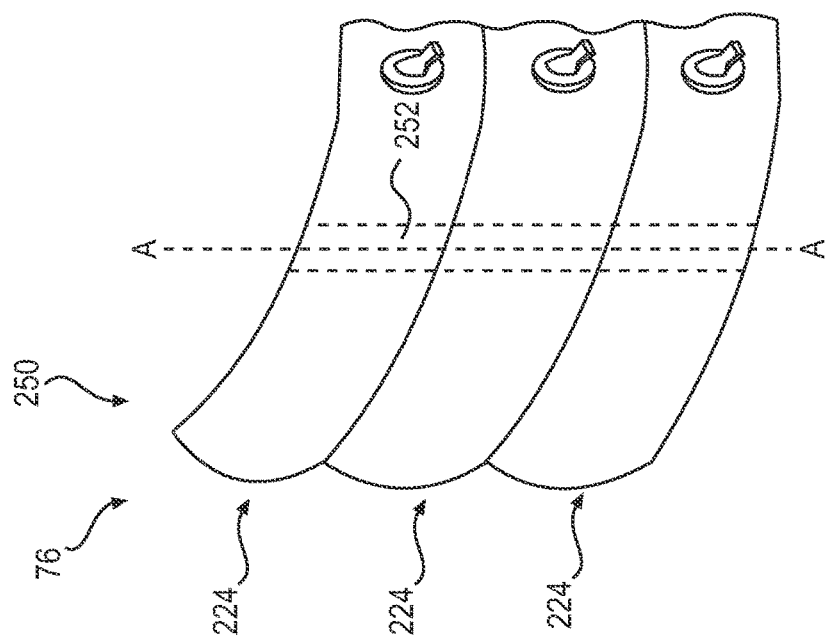
FIG. 19 is a diagram of a portion of a collar of FIGS. 4-7, according to another embodiment.

FIG. 19 is a view of a portion 250 of the collar 76 of FIGS. 4-7 and 14, according to another embodiment.

Figure 20:
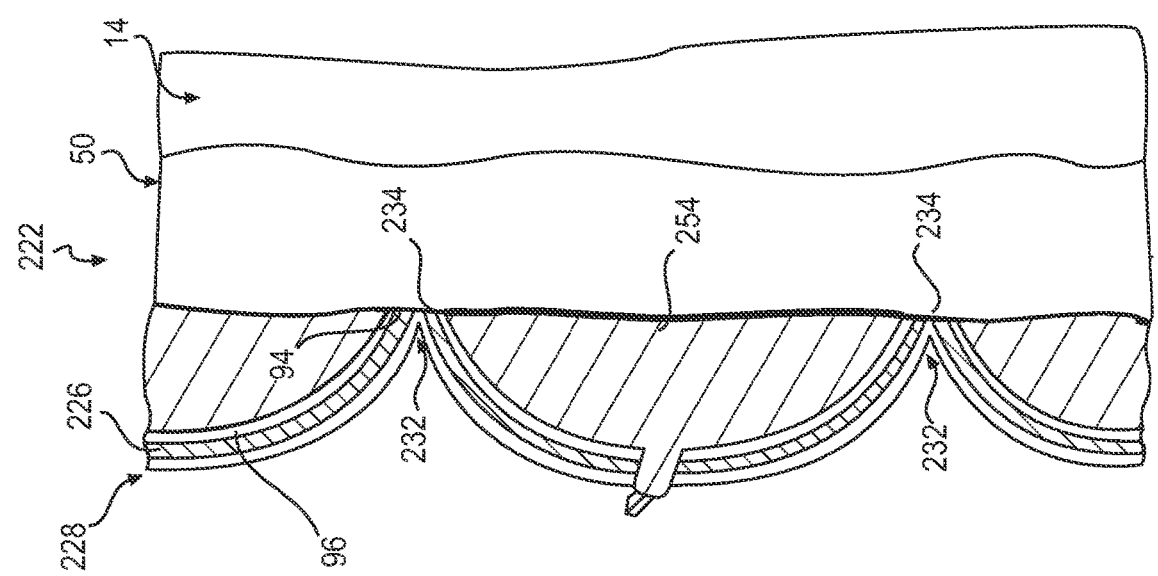
FIG. 20 is a view of the collar portion of FIG. 19 taken along line A-A of FIG. 19, according to an embodiment.

FIG. 20 is a cross-sectional view of the collar portion 250 of FIG. 19 taken along a line A-A of FIG. 11, and of the portion 222 of the subject's neck 50 and airway 14, according to an embodiment.

Referring to FIGS. 19-20, the collar portion 250 is similar to the collar portion 220 of FIGS. 16-18 but for the addition of one or more sealing surfaces 252 that are each transverse to the sealing surfaces 94 away from the terminators 240, and the addition of a corresponding one or more pressure-region separators 254, which may be similar to the terminators 240 and which support the transverse sealing surfaces. The transverse sealing surfaces 252 can be similar to the sealing surfaces 94, and can be attached to the separators 254 in any suitable manner. And the separators 254 can be made from the same material as the frame portions 226 or the terminators 240, and can be attached to the vacuum surface 96 or to the frame portions in a manner similar to the manner in which the terminators can be attached to the vacuum surface or the frame portions as described above in conjunction with FIG. 18. Alternatively, the separators 254 can be formed integrally with the frame portions 226 in a manner similar to the manner in which the terminators 240 can be formed integrally with the frame portions 226 as described above in conjunction with FIG. 18.

The transverse sealing surfaces 252 and separators 254 form additional pressure regions 200 (FIGS. 16-18) by dividing the collar segments 224 into multiple sections.

Furthermore, if the sleep-apnea-treatment system 70 (FIGS. 4-7) regulates the pressures within the pressure regions 200 (FIGS. 16-18) in a manner that mimics peristalsis, the controller 134 (FIG. 8) can be configured to change the pressures within the pressure regions belonging to the same collar segment 224 simultaneously. Alternatively, the controller 134 can be configured to regulate the pressures within the pressure regions 200 in a manner similar to the peristalsis technique described above in conjunction with FIGS. 16-18, but in a circumferential direction (i.e., in a direction around the neck 50 instead of in a direction up or down the neck). Or, the controller 134 system can be configured to so regulate the pressures within the pressure regions 200 both in a transverse direction (i.e., up or down the neck) and in a circumferential direction.

Still referring to FIGS. 19-20, alternate embodiments of the collar 76, and of the system 70 (FIGS. 4-7) in general, are contemplated. For example, the same alternatives discussed above for the collar 76 of FIGS. 16-18 can be applicable to the collar 76 of FIGS. 19-20.

Figure 21:
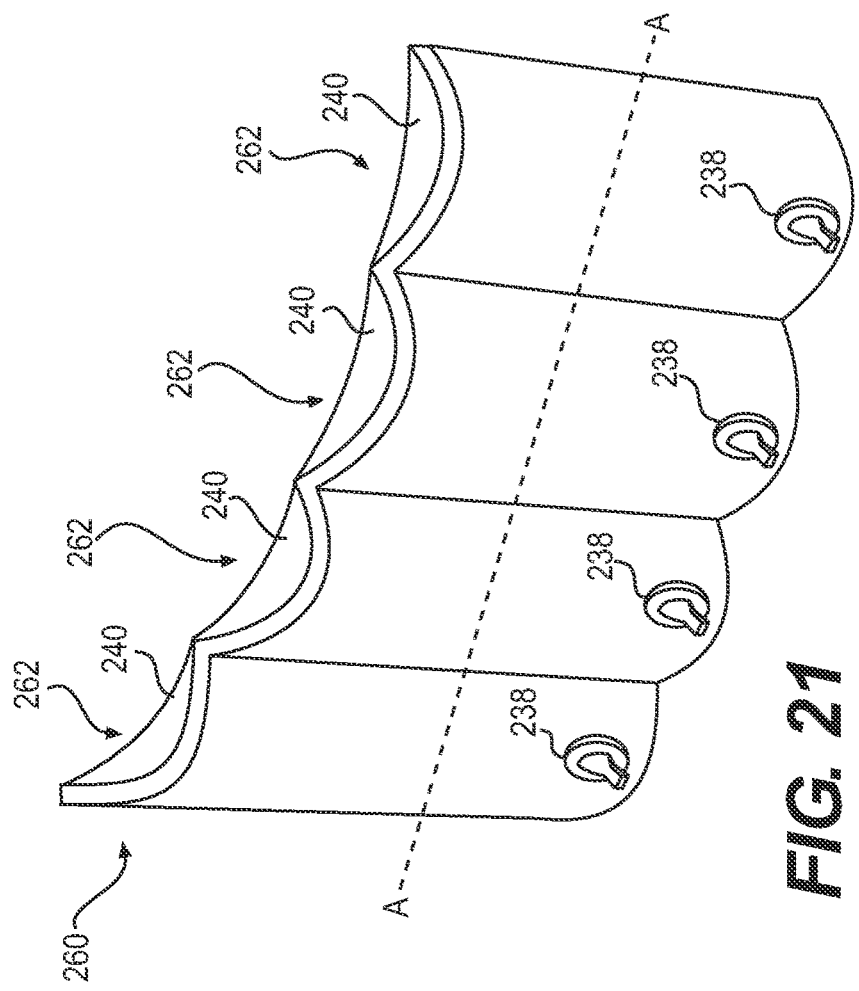
FIG. 21 is a diagram of a portion of a collar of FIGS. 4-7, according to yet another embodiment.

FIG. 21 is a view of a portion 260 of the collar 76 of FIGS. 4-7 and 14, according to yet another embodiment.

Figure 22:
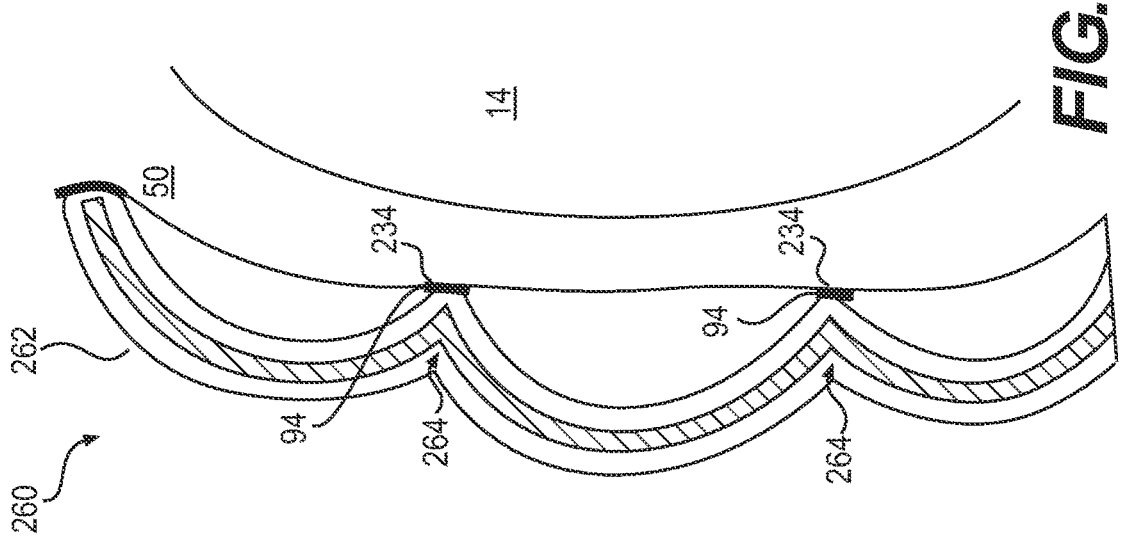
FIG. 22 is a view of the collar portion of FIG. 21 taken along line A-A of FIG. 21, according to an embodiment.

FIG. 22 is a cross-sectional view of the collar portion 260 of FIG. 21 taken along a line A-A of FIG. 21, and of the portion 222 of the subject's neck 50 and airway 14, according to an embodiment.

Referring to FIGS. 21-22, the collar portion 260 is similar to the collar portion 220 of FIGS. 16-18, except that collar segments 262 are configured to extend in a transverse direction (i.e., up/down the neck 50) while the subject 12 (FIG. 4) is wearing the sleep-apnea system 70, unlike the collar segments 224 (FIGS. 16-18), which are configured to extend in a circumferential direction (i.e., around the neck). And although not shown, the collar portion 260 may be similar to the collar portion 250 of FIGS. 19-20 in that it can include sealing surfaces and separators that are similar to the sealing surfaces 252 and the separators 254 and that are approximately transverse to (i.e., in approximately the same direction as the line A-A in FIG. 21) the sealing surfaces 92 and joints 264.

Still referring to FIGS. 21-22, alternate embodiments of the collar 76, and of the system 70 (FIGS. 4-7) in general, are contemplated. For example, the same alternatives discussed above in conjunction with FIGS. 16-20 can be applicable to the collar 76 of FIGS. 21-22.

Figure 23:
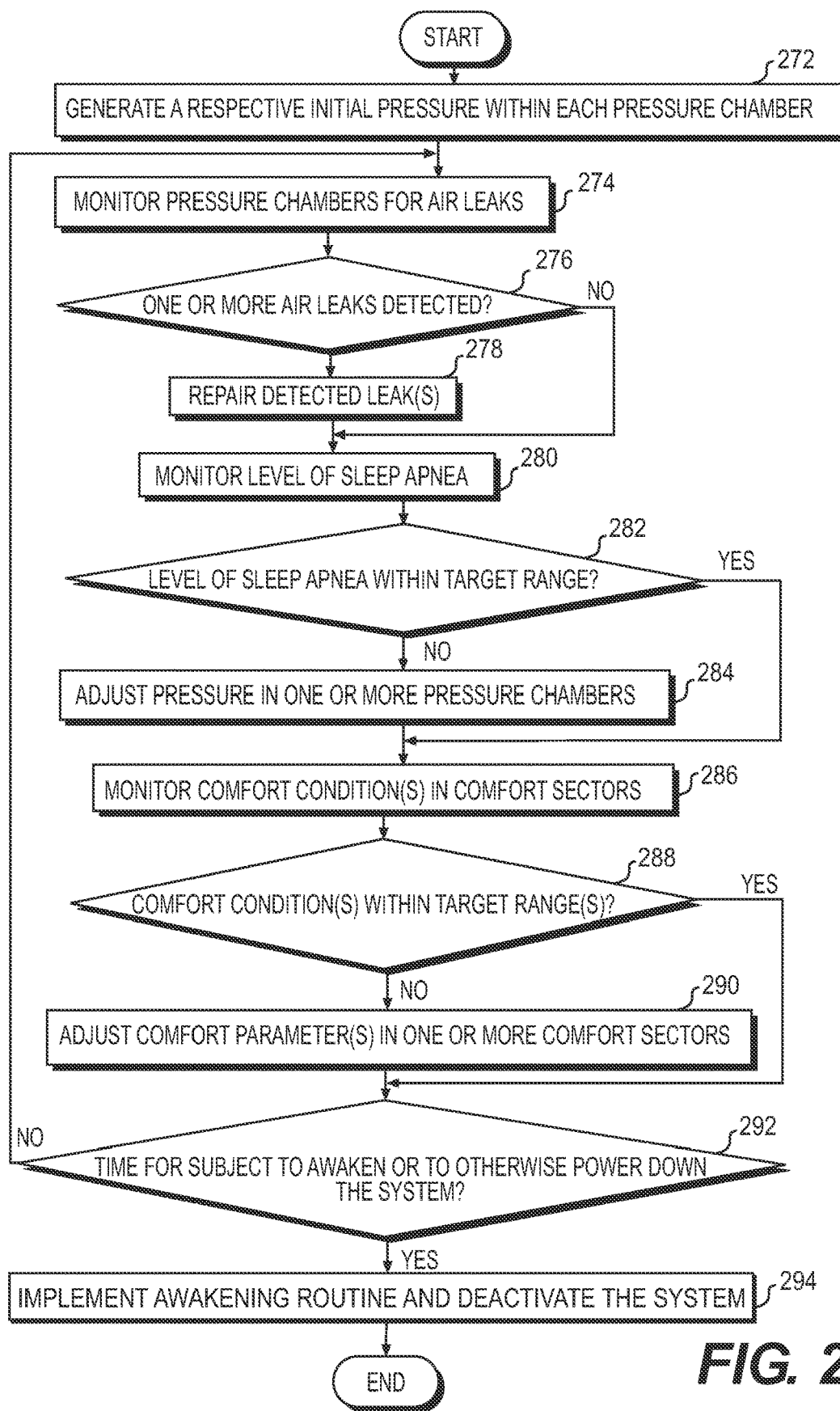
FIG. 23 is a flow diagram of the operation of the sleep-apnea-treatment system of FIGS. 4-7, according to an embodiment.

FIG. 23 is a flow diagram 270 of an operational mode of the sleep-apnea-treatment system 70 (FIGS. 4-7), according to an embodiment.

Referring to FIGS. 4-8, and 14-22, operation of the sleep-apnea-treatment system 70 (FIGS. 4-7) is described, according to an embodiment.

After the subject 12 puts on and activates the treatment system 70 (e.g., via the power-switch assembly 100), at a step 272 of the flow diagram 270, the controller 134 causes the pump assembly 118 and the pressure-regulator assembly 120 to generate a respective initial pressure, for example, a respective negative pressure, within each pressure region 200. That is, the pump assembly 118 generates the one or more negative pressures by drawing air from outside of the collar 76 into the inlet valves 238, through the inlet openings

202, into the one or more pressure regions 100, through the outlet openings 204, through the valve and pressure-regulator assemblies 120 and 122, into the pump assembly 118, and out through the outlet valve 102. Alternatively, one or more of the inlet valves 238 and inlet openings 202 can be inactivated or omitted such that the pump assembly generates at least some of the one or more negative pressures without generating respective sustained airflows.

Next, at a step 274 of the flow diagram 270, the controller 134 monitors the one or more pressure regions 200 for air leaks in response to one or more pressure indications from the pressure-sensor assembly 126.

At a step 276, the controller 134 determines whether there are any air leaks. If the controller 134 determines that there are no leaks, then the controller proceeds to a step 280. But if the controller 134 determines that there is at least one leak, then the controller proceeds to a step 278, At the step 278, the controller 134 causes the repair of each of the detected one or more leaks, for example, by causing the sealant-dispenser assembly 124 to dispense a sealant from the reservoir 146 via one or more of the sealant-dispensing openings 210 in the vicinity of the respective leak.

Then, at the step 280, the controller 134 monitors the degree of sleep apnea that the subject 12 is experiencing via the apnea-degree-sensor assembly 128. For example, the controller 134 can monitor the subject's respiratory rate.

Next, at a step 282, the controller 134 determines whether the degree of sleep apnea that the subject 12 is experiencing is within a target range. For example, the controller 134 may determine whether the subject's respiratory rate is within a target range. If the controller 134 determines that the degree of sleep apnea is within the target range, then the controller proceeds to a step 286. But if the controller 134 determines that the degree of sleep apnea is outside of the target range, then the controller proceeds to a step 284.

At the step 284, the controller 134 identifies one or more pressure regions 200 that the controller has determined are to be adjusted, and controls the pump assembly 118 or the pressure-regulator assembly 120 to adjust the pressure in the identified one or more pressure regions in an effort to drive the degree of sleep apnea toward the target range.

Then, at the step 286, the controller 134 monitors one or more comfort conditions in one or more comfort sectors of the system 70 (FIGS. 4-7). For example, the controller 134 can monitor temperature or pressure in one or more of the pressure regions 200.

Next, at a step 288, the controller 134 determines whether the one or more comfort conditions in one or more comfort sections are within respective target ranges. For example, the controller 134 can determine whether the temperature within each pressure region 200 is within a respective target range. If the controller 134 determines that each of the one or more comfort conditions is within its respective target range, then the controller proceeds to a step 292. But if the controller 134 determines that at least one of the one or more comfort conditions is outside of its respective target range, then the controller proceeds to a step 290.

At the step 290, the controller 134 identifies one or more comfort sectors that are to be adjusted, and controls the temperature-control assembly 132 to adjust one or more comfort parameters (e.g., temperature) in the identified one or more comfort sectors in an effort to drive the one or more comfort conditions toward their respective target ranges. In addition, or in the alternative, the controller 134 may control the pump assembly 118 and the pressure-regulator assembly 120 in a peristalsis manner so as to temporarily reduce the magnitude of the pressure within one or more pressure regions 200 to reduce the chances of an edema forming, or to otherwise give the respective regions 246 of the subject's neck 50 a "break" from the higher-magnitude pressures.

At the step 292, the controller 134 determines whether it is time for the subject 12 to awaken or to otherwise power down the system (e.g., because the subject has removed the system 70 and turned the system "off" via the power-switch assembly 100). If it is not time to awaken the subject 12, then the controller 134 returns to the step 274. But if it is time to awaken the subject 12, then the controller 134 proceeds to a step 294.

At the step 294, the controller 134 implements an awakening routine and then deactivates the system 70 (FIG. 4), or, alternatively, the controller skips an awakening routing and deactivates the system. As example of an awakening routine, the controller 134 can be programmed to help awaken the subject 12 at a specified time, or in response to increasing ambient light, by sounding an audible alarm and slowly reducing the magnitude of the respective pressure within each pressure region 200, or by varying the respective pressure within one or more pressure regions according to a sequence or pattern that gently awakens the subject.

After the step 294, the above-described operational mode ends, and is repeated the next time that the subject 12 activates the sleep-apnea-treatment system 70.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. For example, one or more of the above-described techniques can be implemented in a sleep-apnea-treatment system (e.g., a CPAP system) other than the system 70. Furthermore, one or more of the above-described techniques may be modified for implementation on a system (e.g., a CPAP system) that treats sleep apnea with positive pressure instead of negative pressure. Moreover, it is contemplated that a system may treat sleep apnea with both positive and negative pressure using one or more of the above-described techniques.

While various aspects and embodiments have been disclosed herein, other aspects and embodiments will be apparent to those skilled in the art from the detailed description provided herein. The various aspects and embodiments disclosed herein are for purposes of illustration and are not intended to be limiting, with the true scope and spirit being indicated by the following claims.

What is claimed is:
1. A system, comprising:
a collar configured to be worn on a neck of a subject;
a first sensor mounted to the collar and configured to sense a respective degree to which an airway of the subject is open at each of one or more times;
a second sensor mounted to the collar and configured to sense a condition that is related to the respective degree to which the airway is open at each of the same one or more times; and
a processor coupled to the first and second sensors and configured
to monitor the respective degree to which the airway is open at each of the one or more times,
to monitor the condition at each of the one or more times, to correlate the condition at each of the one or more times to the respective degree to which the airway is open at each of the one or more times, and to generate a data structure that represents the correlation between the condition and the degree to which the airway is open.

2. The system of claim 1 wherein the second sensor is configured to sense as the condition a condition that includes at least one attribute that is related to sleep apnea.

3. The system of claim 1 wherein:
the second sensor comprises a sleep apnea sensor configured to generate a signal in response to a sleep apnea marker of the subject; and
the processor is configured to determine a level of the sleep apnea marker from the signal, and to monitor the condition by monitoring the level of the sleep apnea marker.

4. The system of claim 1, further comprising:
wherein the first sensor is configured to generate a first signal in response to the degree to which the subject's airway is open;
wherein the second sensor is configured to generate a second signal in response to the condition that is related to the degree to which the airway is open;
a sampler configured to sample the first and second signals; and
wherein the processor is configured to correlate the condition to the degree to which the airway is open by correlating a sample of the first signal taken at a time with a sample of the second signal taken at the same time.

5. The system of claim 1, further comprising:
an apparatus coupled to the processor and configured to vary the degree to which the subject's airway is open; and
wherein the processor is configured to cause the apparatus to vary the degree to which the subject's airway is open over a range.

6. The system of claim 1, further comprising:
an apparatus coupled to the processor and configured to vary the degree to which the subject's airway is open by applying positive pressure within the airway; and
wherein the processor is configured to cause the apparatus to vary the degree to which the subject's airway is open over a range.

7. A system for treating sleep apnea, the system comprising:
a collar having a vacuum surface, multiple inlet openings and multiple outlet openings disposed in the vacuum surface, an output portion, and a sealing surface that is configured to form a seal with a region of a neck of a subject having an airway and a throat;
a sensor mounted to the collar, configured to monitor a quantity that is related to the airway, and configured to generate, in response to the quantity, a feedback signal that indicates a degree to which the airway is open; and
a pump mounted to the collar, configured to maintain the airway open by drawing, through the multiple inlet openings and the multiple outlet openings, a vacuum in a space between the vacuum surface and a region of the throat, and configured to adjust a level of the vacuum in response to the feedback signal, the multiple inlet openings being disposed between the outer portion of the collar and the space, the multiple outlet openings being disposed between the space and the pump.

8. The system of claim 7 wherein the sensor is configured to monitor as the quantity a condition of the subject, the condition being dependent upon the degree to which the airway is open, and to correlate the condition to the degree to which the airway is open.

9. The system of claim 7 wherein the sensor is configured to monitor as the quantity a dimension of the airway.

10. A system for treating sleep apnea, the system comprising:
means for opening a subject's airway by generating a negative pressure between a vacuum surface of a collar and the subject's throat;
means for monitoring the subject's airway from outside of the subject's airway, the means for monitoring being mounted to the collar and including no component that is remote from the collar; and
means for adjusting the negative pressure in response to the monitoring to maintain a level of opening of the subject's airway within a predetermined range.

11. The system of claim 10 wherein the means for monitoring the airway comprises:
means for monitoring a value of a transverse dimension of the airway; and
means for determining the level of opening of the airway from the value of the dimension.

12. A collar, comprising:
a vacuum surface that is locatable over a region of a throat of a subject;
a sealing surface disposed around the vacuum surface; and
an apparatus configured to form a releasable seal between the sealing surface and a region of a neck of the subject by automatically dispensing a sealing material via sealant-dispensing openings formed in the sealing surface, the apparatus including no component remote from the collar.

13. The collar of claim 12 wherein the apparatus is configured to treat an obstruction in an airway of the subject.

14. A system, comprising:
means for maintaining a releasable seal around a vacuum surface of a collar between a sealing surface of the collar and a region of a neck of a subject by automatic delivery of a sealing material to the sealing surface, the vacuum surface locatable over a region of a throat of the subject, all components of the means for maintaining secured to the collar; and
means for opening an airway of the subject by drawing a vacuum between the vacuum surface of the collar and the region of the throat.

15. The system of claim 14 wherein the means for maintaining the seal comprises means for exuding the sealing material between the sealing surface and the neck region.

16. The system of claim 14 wherein the means for maintaining the seal comprises means for transporting the sealing material from a reservoir to between the sealing surface and the neck region.

17. The system of claim 14, further comprising means for detecting a leak in the seal.

18. The system of claim 14, further comprising:
means for detecting a leak in the seal; and
wherein the means for maintaining the seal comprises means for automatically repairing the leak.

19. The system of claim 14, further comprising:
means for detecting a leak in the seal; and
wherein the means for maintaining the seal comprises means for automatically repairing the leak in response to the means for detecting the leak.

20. A system for treating sleep apnea, the system comprising:

a collar having a vacuum surface, multiple inlet openings and multiple outlet openings disposed in the vacuum surface, and a sealing surface that is configured to form a seal with a region of a neck of a subject having an airway and a throat;

a sensor mounted to the collar, configured to monitor a quantity that is related to the airway, and configured to generate, in response to the quantity, a feedback signal that indicates a degree to which the airway is open; and a pump mounted to the collar, configured to maintain the airway open by drawing, through the multiple inlet openings and the multiple outlet openings, a vacuum in a space between the vacuum surface and a region of the throat, and configured to adjust a level of the vacuum in response to the feedback signal, the multiple inlet openings being disposed between a region external to the collar and the space, the multiple outlet openings being disposed between the space and the pump.

* * * * *